United States Patent [19]
Haynes et al.

[11] Patent Number: 6,048,715
[45] Date of Patent: Apr. 11, 2000

[54] TWO-PHASE PARTITION AFFINITY SEPARATION SYSTEM AND AFFINITY SEPARATED CELL-CONTAINING COMPOSITION

[75] Inventors: Charles A. Haynes; Peter Tomme; Douglas G. Kilburn, all of British Columbia, Canada

[73] Assignee: Univ. of British Columbia, Vancouver, Canada

[21] Appl. No.: 08/685,808

[22] Filed: Jul. 24, 1996

Related U.S. Application Data

[63] Continuation-in-part of application No. 08/505,860, Jul. 24, 1995, which is a continuation-in-part of application No. 08/249,037, May 24, 1994, which is a continuation of application No. 07/865,095, Apr. 8, 1992, Pat. No. 5,340,731, which is a continuation-in-part of application No. 07/603,987, Oct. 25, 1990, Pat. No. 5,202,247, which is a division of application No. 07/216,794, Jul. 8, 1988, Pat. No. 5,137,819.

[51] Int. Cl.[7] .......................... C12N 11/12; C12N 15/00; C12P 21/06; A23J 1/00
[52] U.S. Cl. ...................... 435/179; 435/68.1; 435/69.1; 435/69.7; 435/70.1; 435/71.1; 435/395; 435/803; 435/815; 435/71.2; 435/172.3; 435/178; 435/320.1; 530/413; 530/813; 530/814; 436/529; 436/530
[58] Field of Search ....................................... 530/413, 415, 530/813, 814; 435/174, 177, 178, 179, 68.1, 69.1, 69.7, 70.1, 71.1, 71.2, 172.3, 320.1, 395, 803, 815; 436/529, 530

[56] References Cited

U.S. PATENT DOCUMENTS

| | | | |
|---|---|---|---|
| 5,137,819 | 8/1992 | Kilburn et al. | 435/179 |
| 5,202,247 | 4/1993 | Kilburn et al. | 435/195 |
| 5,340,731 | 8/1994 | Kilburn et al. | 435/179 |

OTHER PUBLICATIONS

Coutinho et al., *FEMS Microbiol. Lett.* (1993) 113: 211–218.
Coutinho et al., *Mol. Micobiol.* (1992) 6: 1243–1252.
Coutinho et al., *Mol. Micobiol.* (1991) 5: 1221–1233.
Gilkes et al., *Microbiol. Rev.* (1991) 55: 303–315.
Graham et al., *Gene* (1995) 158: 51–54.
Graham et al., *Nucleic Acids Res.* (1993) 21: 4923–4928.
Greenwood et al. *Biotechnol. Bioeng.* (1994) 44: 1295–1305.
Miller et al., *Proc. 6th Int. Conf. on Biotechnology in the Pulp and Paper Industry.* (1995) 11–15.
Moser et al., *Appl. Environ. Microbiol.* (1989) 55: 2480–2487.
Skuse et al. *Enzyme Microb. Technol.* (1992) 14 785–790.
Wierzba et al., *Biotechnol. Bioeng.* (1995) 47: 147–154.
Wierzba et al., *Biotechnol. Bioeng.* (1995) 46: 185–193.
Johansson et al CA–98:193917.
Ong et al CA:122:312495.

*Primary Examiner*—David M. Naff
*Attorney, Agent, or Firm*—Rae-Venter Law Group, P.C.

[57] ABSTRACT

A two-phase partition system is provided for affinity separation of a composition containing a polysaccharide binding peptide from a mixture such as a fermentation broth. The peptide may be from an enzyme and lacking in polysaccharidase activity such as the binding domain of cellulase that binds to cellulose. The system contains a phase-forming oligosaccharide polymer such as a cellulose derivative to which the peptide binds with a Ka of $10^3$ M to $10^7$ M, and a phase inducing agent such as a polyethylene glycol polymer, or a salt present at sufficiently high concentration to induce phase separation. If the oligosaccharide polymer is thermoseparating, phase separation can be induced by heating. Using the system involves contacting a composition containing the peptide such as a fusion protein with the system, partitioning the composition into a phase containing the oligosaccharide polymer by binding to the polymer and recovering the polymer containing the bound composition. The peptide or a fusion protein containing the peptide can be contacted with a cell having a carbohydrate residue to which the peptide binds to form a complex, and the complex is separated with the system to produce a bound cell composition. The peptide may be linked through a protease recognition sequence to a macromolecule such as an enzyme, a hormone or an antibody, and the macromolecule can be removed by using a protease to cleave the recognition sequence.

22 Claims, 18 Drawing Sheets

```
CfiCenC(N1)...ASPIGEGTTFDDG-PEGWVAYGTDGPLDTSTGALCVAVPAGSAQ-YGVGVVL
CfiCenC(N2)...VELLPH-TSFAE-SLGPWSLYGTSEPVF-ADGRMCVDLPGGQGNPWDAGLVY
CceCelCCE....V-GLPWHVVESYPAKASFEITSDGKYKITAQ-KI-GEA--GKGERWDIQFRH
MxaEGL.......LTELVSNGTFNGGTVSPWWSGPNTQSRVENARLRVDVGGGTANP-WDALIGQ
SriCel1......VEQVRNGT-FDT-TTDPWW-TS-NVTAGLSDGRLCADVPGGTTNRWDSAIGQ
TfuE1........VNQIRNGD-FSSGT-APWWGTE-NIQLNVTDGMLCVDVPGGTVNPWDVIIGQ

CfiCenC(N1)...NGVAIEEGTTYTLRYTATAS-TDVTTVRALVGQNGAPYGTVLDTSPA-LTSE
CfiCenC(N2)...NGVPVGEGESYVLSFTASAT-PDMPPVRVLVGEGGGAYRTAFEQGSAPLTGE
CceCelCCE....RGLALQQGHTYTVKFTVTASRACKIYPK--IGDQGDPYDEYWNMNQQWNFLE
MxaEGL.......DDIPLVNGRAYTLSFTASAS--VSTTVRVTVQLESAPYTAPLDR-QITLDGT
SriCel1......NDITLVKGETYRFSFHASG-IPEGHVVRAVVGLAVSPYDTWQEASPV-LTEA
TfuE1........DDIPLIEGESYAFSFTASSTVPV--SIRALVQEPVEPWTTQMDERAL-LGPE

CfiCenC(N1)...-----PRQVTETFTASATYPATPAADDPEGQIAFQLGGF------------S
CfiCenC(N2)...-----PATREYAFTSNLT---FPPDGDAPGQVAFHLG--------------K
CceCELCCE....LQANTPKTVTQTFTQTK-------GDKKNVEFAFHLAPDKTTSEAQNPASFQ
MxaEGL.......-----SRRFTPPFTSTLA--------TQAGQVTFQMGGRA-----------T
SriCel1......-----DGSYSYTFTAPV--------DTTQGQVAFQVGG-------------S
TfuE1........-----AETYEFVFTSNV--------DWDDAQVAFQIGG-------------S

CfiCenC(N1)...ADAWTFCLDDVAL--
CfiCenC(N2)...AGAYEFCISQVSL--
CceCELCCE....PITYTF--DEIYIQD
MxaEGL.......-GFSAF-IDDISL--
SriCel1......TDAWRFCVDDVSLLG
TfuE1........DEPWTFCLDDVALLG
```

FIG. 1

```
         g10 leader                       NcoI EcoRI              MCS                       HindIII
                           rbs           M  E  F  E  L  G  T  R  G  S  S  R  V  D  L  Q  A  C  K  L
 XbaI
AtctagaAATAATTTGTTTAACTTTAAGAaggaGATATATccatggaattcgaGAGCTCGGTACCCGGGGATCCTCTAGAGTCGACCTGCAGGCATGCAAGCTT
TagatctTTATTAAACAAATTGAAATTCTcctCTATATAggtacctTAAGCTCTCGAGCCATGGGCCCCTAGGAGATCTCAGCTGGACGTCCGTACGttcgaa

FIG. 2A

FXa  StuI  EcoRI             mcs
                                                         P  T  P  I  E  G  R  P  E  F  Q  L  G  T  R  G  S  S
         rbs           M  S  T  R  (CBD)                 CCCACGCCGATCGAGGGCaggcctgaattcCAGCTCGGTACCCGGGATCCTCT
                                                         GGGTGCGGCTAGCTCCCGtccggacttaagGTCGAGCCATGGGCCCCTAGGAGA

FIG. 3A g10 leader         SacI
                           rbs          M  S  T  R
 TTTAACTTTAAGAaggagctcCTTGATGTCCACCGC.......
 AAATTGAAATTCTcctcgagGAACTACAGGTGGGCG.......

HindIII
 R  V  D  L  Q  A  C  K  L
 AGAGTCGACCTGCAGGCATGCaagctt
 TCTCAGCTGGACGTCCGTACGttcgaa
```

วันที่ 1

TWO-PHASE PARTITION AFFINITY SEPARATION SYSTEM AND AFFINITY SEPARATED CELL-CONTAINING COMPOSITION

CROSS-REFERENCE TO RELATED APPLICATIONS

This application is a continuation-in-part of U.S. application Ser. No. 08/505,860, filed Jul. 24, 1995, which is a continuation-in-part of U.S. Ser. No. 08/249,037, filed May 24, 1994, which is a continuation of U.S. Ser. No. 07/865,095, filed Apr. 8, 1992, now U.S. Pat. No. 5,340,731 which is a continuation-in-part of U.S. Ser. No. 07/603,987, filed Oct. 25, 1990, now U.S. Pat. No. 5,202,247 which is a division of U.S. Ser. No. 07/216,794, filed Jul. 8, 1988, now U.S. Pat. No. 5,137,819 which disclosures are incorporated herein by reference.

INTRODUCTION

Technical Field

This invention relates to methods for separating and/or concentrating polypeptides and other compounds by affinity phase separation using a polymer-ligand pair in which the ligand binds to a soluble phase-forming oligosaccharide. The invention is exemplified by the use of a phase separation system comprising a soluble oligosaccharide with affinity for a compound comprising as the affinity ligand a cellulose-binding domain from a *Cellulomonas fimi* cellulase.

Background

Production of proteins by expression in microbial systems has become a significant source of high value, medically important proteins. Purification and recovery of recombinant proteins are major considerations in the design of a fermentation process. While traditional means of protein purification can be used to isolate a product, more recently, aqueous two-phase extraction systems have received considerable industrial interest as a means to simplify large-scale purification of protein products, including high-dose therapeutics such as insulin, and industrial proteins such as 3-oxosteroid isomerase, alcohol dehydrogenase, and phosphofructokinase. As a result, a wide variety of two-phase systems are now available for both protein-purification and cell-separation applications. Extraction in aqueous two-phase systems offers unique advantages for large-scale processing of recombinant proteins and peptides, including high activity yields (i.e., the largely aqueous environment minimizes protein inactivation during purification), fast approach to equilibrium, easy scale-up and, most importantly, continuous processing.

Technical feasibility of aqueous two-phase partition systems has been demonstrated in several systems up to the 100,000 L scale. They are formed by adding to water either two water-soluble but incompatible polymers or a water-soluble polymer and a strong electrolyte. Polyethylene glycol (PEG) serves as one of the polymer components in many industrial two-phase systems due to its low price and availability in a wide range of molecular-weight fractions. Fractionated dextran, an α-1, 6 glucosaccharide with α-1, 3 branching, often serves as the second polymer. However, many other water-soluble polymers are also in use, including a number of other carbohydrate polymers. Aqueous two-phase systems contain mainly water, with each phase enriched in one of the separation-inducing components and nearly devoid of the other. When a mixture of proteins and other biomacromolecules from a fermentation broth is added to an aqueous two-phase system, each type of protein partitions uniquely based on its relative affinity for the two phase-forming components, as well as on its size, surface chemistry, and net charge.

Relatively low partition coefficients and lack of selectivity in conventional aqueous two-phase systems have motivated the development of affinity partition systems which combine the versatility of conventional partition systems with the unique binding selectivity of affinity ligands. In most cases, the biospecific ligand is covalently linked to one or both ends of a phase-forming polymer, usually PEG. The strong partitioning of the polymer during phase formation then causes the accumulation of ligand into one of the equilibrium phases. This highly asymmetric partitioning, combined with the strong affinity of the target protein for the ligand, is the basis behind the affinity separation and concentration.

However, although current affinity partition systems are of some industrial use, they are limited in their capacity and resolving power by low ligand densities which result from the presence of only one or two ligands per polymer chain. Since polymer concentrations are usually less than 15 wt %, affinity partition systems with a 1:1 or 2:1 ligand to polymer stoichiometry usually yield target protein separation factors (relative to those of the contaminants) between 5 and 50. While these separation factors are more than sufficient for product concentration, they do not generally provide a desired product purity in a cost-effective, one or two-stage extraction process. Classic affinity partition systems also are limited by the expense of the chemistry needed to produce the polymer-ligand conjugates. For example, conjugation of a ligand to PEG first requires substitution of the terminal hydroxyl groups with more reactive electrophiles, such as bromides, chlorides, or epoxides. A second nucleophilic-attack reaction is then required to covalently bind the polymer and ligand. The ligand polymer conjugates also must be designed specifically for each protein or class of proteins to be purified.

A recent development in aqueous biphasic separations is to combine aqueous two-phase systems with temperature-induced phase separation. To date, these systems have used a thermoseparating polymer as the top-phase polymer with either dextran or hydroxypropyl starch as the bottom-phase polymer. Temperature-induced phase separation following the purification step then makes it possible to separate and recycle the polymer from the biological products. In this form, the process has the advantage of recovering the thermoseparating polymer, but suffers from the distinct disadvantage that the target protein has no unique and strong affinity for the thermoseparating polymer. Application of oligosaccharide binding domain technology to these two-phase systems would allow for a high-affinity separation to the phase containing the polymer to which the domain binds followed by a simple method for recovering and recycling the polymer. It therefore is of interest to develop rapid, inexpensive, high capacity methods for purification of a desired protein, particularly to develop methods which can use generic polymer-ligand conjugates.

Relevant Literature

For a review of phase-forming oligosaccharides, see Zaslavsky, *Aqueous Two-Phase Partitioning*, Marcel Dekker, Inc.: New York (1995); Albertson, Pa., *Partitioning of Cell Particles and Macromolecules*, 3$^{rd}$ ed., Wiley Interscience: New York (1986); Walter, H. Brooks, D. E., and Fisher, D., *Partitioning in Aqueous Two-Phase Systems*, Academic Press: Orlando, Fla. (1985).

The following references relate to thermoseparating polymers: Malcolm, and Rowlinson, (1957). *Trans. Faraday Soc.*, 53,921; Bailey and Callard, (1959). *J. Appl. Polym*, 1, 56; Horne, et al. *J. Colloid Interface Sci.*, 35, 77; Saeki, et al. *J. Chem Soc. Faraday Trans.* 1, 79, 975; Fujishige, et al. (1989) *J. Phys. Chem*, 93, 3311; Galeav and Mattiasson, (1993). *Enzyme Microb. Technol.*, 15, 354; and Chen and Hoffman, (1995). *Nature*, 373, 49.

References relating to endoglucanase C include the following. Moser et al., *Applied and Environmental Microbiology* (1989) 55:2480–2487; *Molecular Microbiology* (1991) 5:1221–1233; Coutinho, et al., *Molecular Microbiology* (1992) 6:1243–1252; and Coutinho, et al. *FEMS Microbiology Letters* (1993) 113:211–218. For a review of β-1, 4-glycanases, see Gilkes, et al. (1991) *Microbial Reviews* 55:303–315. Also, see Miller, Jr., et al. (1995) *Proc. 6th Int. Conf. on Biotechnology in the Pulp and Paper Industry*, Vienna, Austria.

SUMMARY OF THE INVENTION

Aqueous phase separation and/or purification systems, together with methods for their preparation and use, are provided which are based on polymer-ligand conjugates wherein the polymer is an oligosaccharide polymer and the composition to be separated and/or purified comprises a ligand which binds to the oligosaccharide polymer. The ligand is a polysaccharide binding peptide (PBP) which is an amino acid sequence characterized as capable of binding to a phase-forming oligosaccharide polymer. The composition generally is a fermentation broth, a cell lysate, a biological fluid, or other fluid containing a compound comprising a macromolecule or chemical moiety of interest fused to a PBP. The phase separation system includes one or more phase-forming oligosaccharide polymer and a phase-inducing polymer, another phase-inducing agent or a means for inducing phase separation. The method involves contacting the phase separation system with the composition, which partitions into the oligosaccharide polymer phase, following induction of phase separation and isolating the composition. The composition may be removed from the oligosaccharide polymer with a removal solution having low ionic strength, high pH or containing a chaotropic agent. Alternatively, a specific or non-specific protease can be used for enzymatic removal of the compound from the polysaccharide binding moiety which remains bound to the oligosaccharide polymer by incorporating a protease recognition sequence between the compound and the polysaccharide binding moiety. Where a protease is used, it can be provided bound to a second polysaccharide binding moiety having affinity for a crystalline polysaccharide to which the first polysaccharide binding moiety has no affinity. Optionally, the protease can be recycled by subsequent elution from the solid polysaccharide. Alternatively, the protease bound to the second polysaccharide binding moiety can be provided bound to a solid polysaccharide support to which the polysaccharide binding peptide does not bind. The invention finds use for separation and/or purification of proteins and other compounds which can be joined to a PBP.

BRIEF DESCRIPTION OF THE DRAWINGS

FIG. 1 shows the consensus sequence for cellulose-binding domains based upon the amino acid sequence alignments of the cellulose-binding domain (N1 and N2) of the *Cellulomonas fimi* endoglucanase C (CenC) (SEQ ID NO:1 and SEQ ID NO:2) (Coutinho et al. *Mol. Microbiol.* (1991) 5:1221–1233) and the putative cellulose-binding domains of CceCelCCE (SEQ ID NO:3) (a cellulase from *Clostridium cellulolyticum*) Bagnarda-Tardif et al. *Gene* (1992) 119:17–28), MxaEgl (SEQ ID NO:4) (a β-1,3-glycanase from *Myxococcus xanthus*) (Quillet et al. *Gene* (1995) 158:23–29), SreCell (SEQ ID NO:5) (a cellulase from *Streptomyces reticuli*) Schlochttermeier et al. *Mol. Microbiol.* (1992) 6:3611–3621), and TfuEl (SEQ ID NO:6) (a β-1,4-endoglucanase from *Thermomonospora fusca*) Lao et al. *J. Bacteriol.* (1991) 173:3397–3407). Amino acid residues are indicated in single letter code. A dash (-) indicates a gap left to improve the alignment.

FIGS. 2A and 2B show a graphic representation of the pTugA vector which is used for expression of $PBD_{N1}$ in *Escherichia coli*. Use of pTugA results in high level inducible transcription, enhanced RNA translation, portability, high copy number, stability and versatility. The pTug vectors contain the mutant pMB1 ori derived from pUC13 to enhance copy number (Minton et al. Focus (1988) 10:56), a strong and highly inducible (by IPTG) tac promotor ($P_{tac}$) which is strongly repressed by LacIq The lacIq allele is incorporated in the pTug vector to maintain a constant ratio of $P_{tac}$ to lacIq, ensuring adequate levels of repressor irrespective of the *E. coli* host. The gene10 translational enhancer (Olins et al. *Gene* (1988) 73:227) is also incorporated in the pTug vector. The leader sequence of the endoglucanase A (CenA) from *C. fimi* was incorporated into the vector to allow recovery of a recombinant polypeptide from *E. coli* supernatants. FIG. 2A shows the nucleotide (SEQ ID NO:14) and encoded amino acid (SEQ ID NO:7) sequence of the NcoI-HindIII region as well as the nucleotide sequence of the region upstream of the NcoI site, including the gene 10 translational enhancer ("g10") and the CenA leader sequence ("leader"). FIG. 2B shows the pTugA vector map.

FIGS. 3A and 3B show a graphic representation of the pTugAS vector. FIG. 3A shows the 5' nucleotide (SEQ ID NO:8) and encoded amino acid (SEQ ID NO:9) and the 3' nucleotide (SEQ ID NO:10) and encoded amino acid (SEQ ID NO:11) sequences of the SacI-HindIII region as well as the nucleotide sequence of the region upstream of the SacI site. FIG. 3B shows the pTugAS vector map.

FIG. 9A compares binding in the presence (+) and in the absence (−) of barley β-glucan; FIG. 9B compares binding in the presence (+) and in the absence (−) of hydroxyethyl cellulose, and FIG. 9C compares binding in the presence (+) and in the absence (−) of birchwood xylan.

FIG. 10A shows pTZ-JC2 containing the gene fragment encoding the whole CenC, which was used to obtain the fragment encoding $PBD_{N1}$. FIG. 10B shows vector pUC18-1.6 cenA_PT, which was used to obtain the CenA encoding fragment.

In FIG. 12A, aliquots of buffer containing 25 µg (lanes 2 and 3), 100 µg (lanes 4 and 5), or 250 µg (lanes 6 and 7) of both polypeptides were incubated with bacterial mnicrocrystalline cellulose (BMCC (+)) or without bacterial microcrystalline cellulose (BMCC(−)). In FIG. 12B, supernatants containing the unadsorbed fractions from the BMCC incubation mixtures were further incubated with phosphoric acid swollen cellulose (PASC(+)). Results with control samples without addition of (PASC(−)) also are shown.

FIG. 13A shows fed-batch production, purification, and immobilization of the fusion protein. FIG. 13B shows use of the fusion protein for hydrolysis of cellulosic materials to glucose with a reusable fermentor-immobilization column setup.

FIG. 18 shows experimental cloud-point diagram for UCON 50-HB-5100 in water and in 100 mM citrate buffer. For a 10° (w/w) UCON solution, phase separation occurs at 323 K in the binary mixture and at 312 K in the buffer-containing system.

DESCRIPTION OF THE SPECIFIC EMBODIMENTS

Figure 2B:
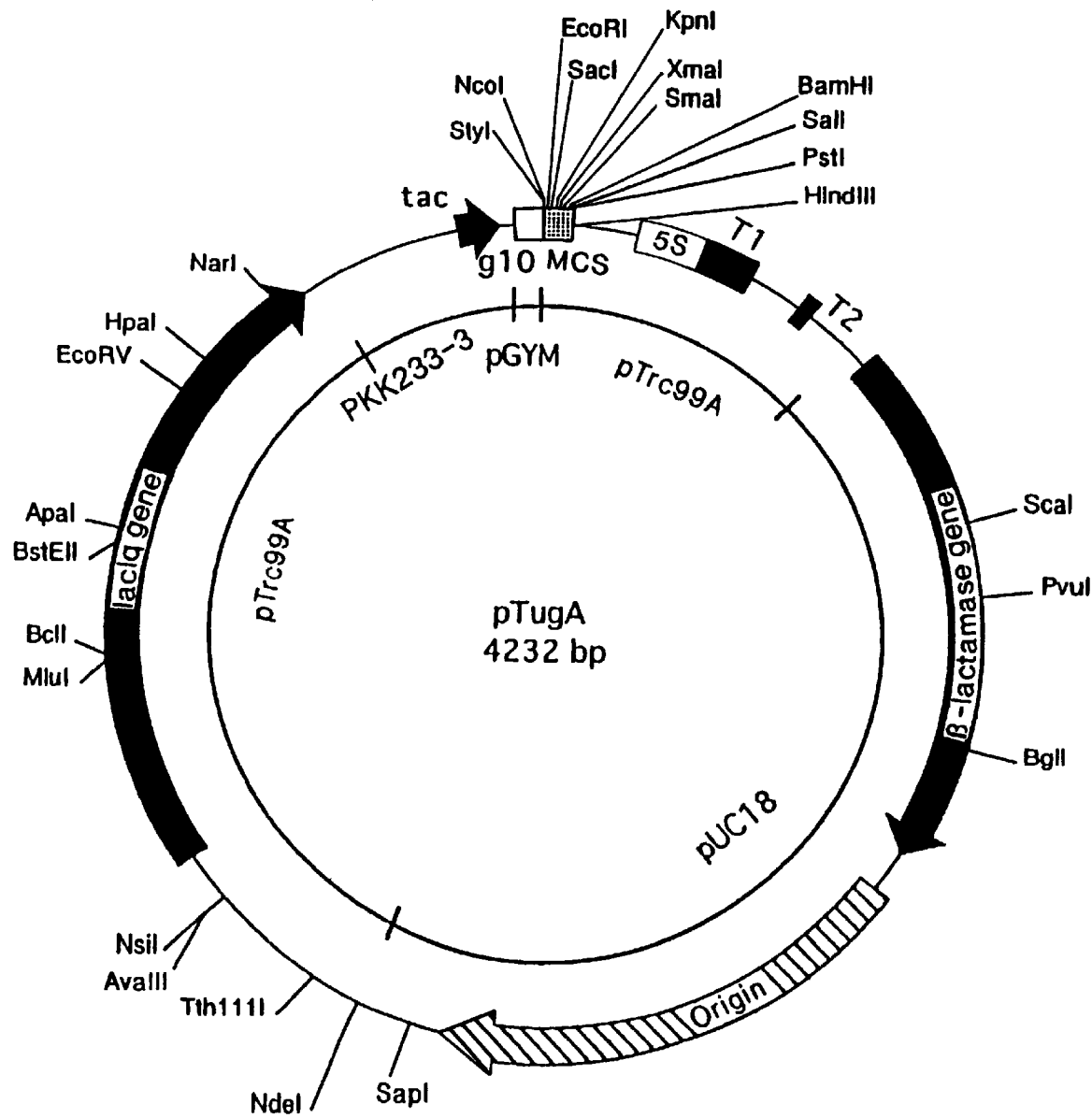
Figure 3B:
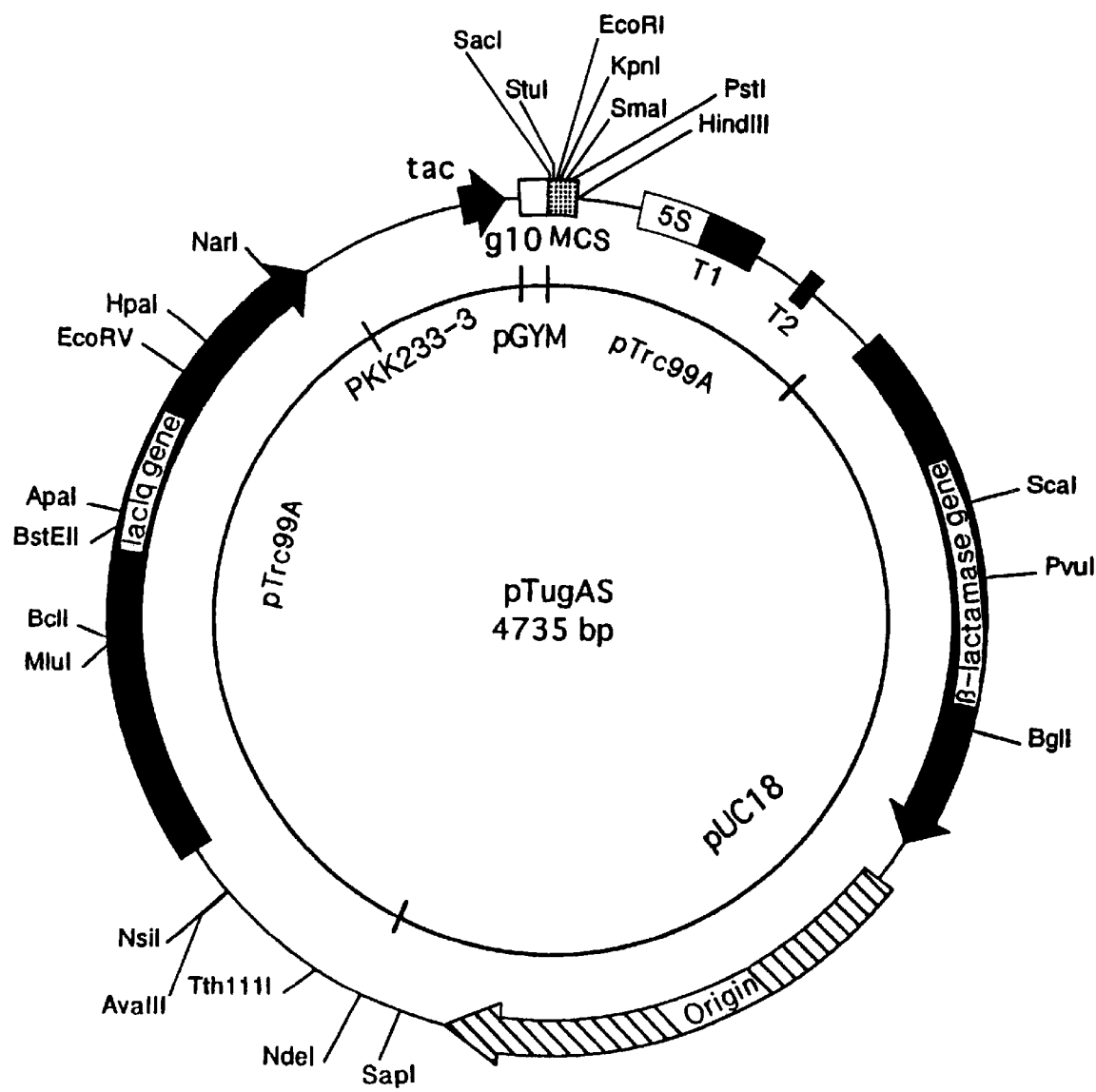
Figure 4:
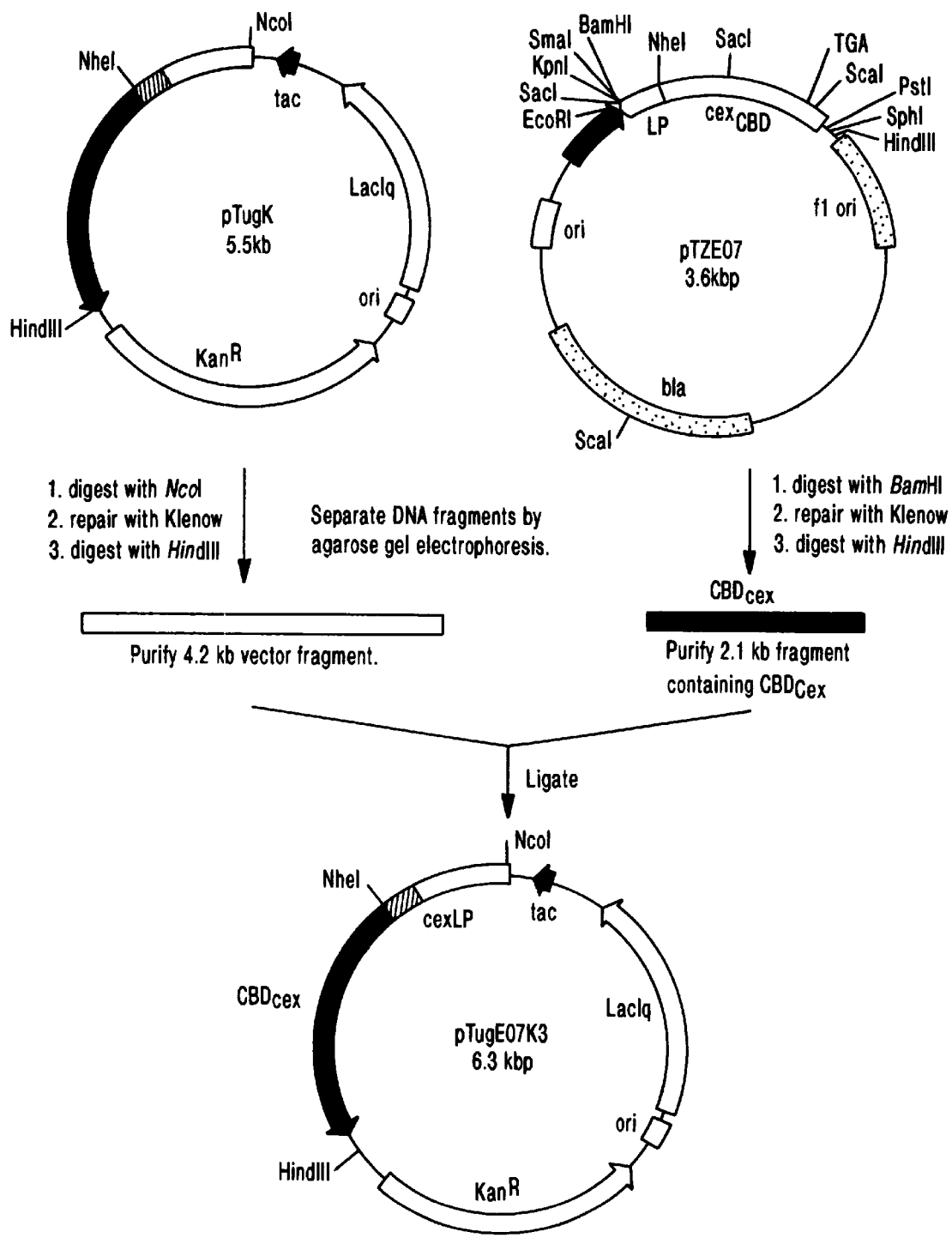
FIG. 4 shows the construction of pTugEO7K3. pTugK, a derivative of pTugA, caries the selective marker for kanamycin resistance in place of the selective marker for ampicillin resistance, was digested completely with NcoI. The staggered end was repaired with the *Escherichi coli* DNA polymerase I (Klenow fragment) to create a blunt ended restriction site. The modified pTugK vector was then digested completely with HindIII and the 4.2 kbp fragment was isolated. pTZE07 (Ong et al. *Biotechnol. Bioeng.* (1993) 42:401–409) was digested completely with BamHI and the staggered end was repaired with the *Escherichi coli* DNA polymerase I (Klenow fragment) to create a blunt ended restriction site. The modified pTZE07 was then digested completely with HindIII and the 2.1 kbp fragment was isolated. The 4.2 and 2.1 kbp fragments were ligated to give pTugE07K3.

Aqueous phase separation systems which can be used for purification and/or separation of compositions which bind to a phase-forming oligosaccharide polymer are provided. Generally, the compositions include a polysaccharide binding peptide (PBP) comprising an amino acid sequence which has high affinity for the oligosaccharide polymer, such as a polysaccharide-binding domain (PBD) of a polysaccharidase, conjugated to a polypeptide or chemical moiety of interest. However, the polysaccharide binding peptide can include any amino acid sequence which binds to the oligosaccharide polymer. Methods for the preparation of PBPs also are provided; where the PBP can be derived from a PBD of a polysaccharidase, a binding domain of a polysaccharide binding protein or a protein designed and engineered to be capable of binding to a polysaccharide. The PBP can be naturally occurring or synthetic. Where the PBP is a PBD or is derived from a PBD, the amino acid sequence generally is essentially lacking in the hydrolytic enzymatic activity of the polysaccharidase, but retains the substrate binding activity.

The phase separation system generally comprises two phases which are generated by the incompatibility of the components of the phase separation system upon mixing of the components. One component of the system is a phase forming oligosaccharide and a second component is a phase-inducing agent, such as a second polymer, which is incompatible with the oligosaccharide polymer, or a strong electrolyte, particularly a salt, such as a sulfate or citrate salt, which is present at a sufficiently high concentration to induce phase separation. In instances where the phase forming oligosaccharide is a thermoseparating polymer, phase separation can be induced by heating the composition containing the compound to be purified and the phase-forming polymer until phase separation occurs.

The steps of using the phase partition system include contacting composition comprising the polysaccharide binding peptide with the phase separation system. The phase partitioning system can be already mixed, or the composition can be added to a dry form (e.g., lyophilized) of either of the components. As an example, the oligosaccharide polymer is added to the composition thereby rehydrating the polymer and phase separation is induced. For some applications, more than two phases can be used. After a time sufficient for the composition to partition into the oligosaccharide polymer phase, the phases are separated. Partitioning (nonaffinity) of contaminant proteins into the polysaccharide-rich phase is minimized by adjusting the system pH, polymer concentrations, and addition of partitioning electrolytes. Under optimal conditions of operation, multistage contacting of the two aqueous phases then provides either complete or partial (but sufficient) purification of the target composition.

The composition comprising a polypeptide or chemical moiety of interest can be removed from the polymer by contacting the polymer with a removal solution capable of eluting the composition comprising the PBP from the polymer or the composition comprising the PBP can be removed enzymatically by including a protease recognition site or chemical cleavage site between the compound and the PBP. In the latter method of removal, the PBP remains bound to the oligosaccharide polymer. Examples of recognition sites include those for collagenase, thrombin, and Factor Xa which are cleaved specifically by the respective enzymes. Chemical cleavage sites sensitive, for example, to low pH or cyanogen bromide, can also be used.

For ease of removal, the specific cleavage enzyme can be provided as a leavage enzyme complex wherein the cleavage enzyme is bound to a PBP which has substrate binding characteristics which differ from those of the PBP which binds to the soluble oligosaccharide polymer or which binds to a different polysaccharide rather than just different physical forms of the same polysaccharide. Preferably the second PBP binds to an insoluble polysaccharide to which the first PBP does not bind. The insoluable polysaccharide can be added to the mixture containing the compound of interest to remove the cleavage enzyme complex from the solution. Following separation from the solution, the cleavage enzyme complex can be removed from the insoluble polysaccharide and reused. Alternatively, the cleavage enzyme complex can be provided already bound to an insoluble polysaccharide, for example in the form of a column through which the mixture containing the compound of interest is passed.

The subject invention offers several advantages over currently used aqueous phase separation systems. Oligosaccharide polymers including carbohydrate polymers it such as cellulose and other β-glucans, such as those obtained from oat and barley, are plentiful and inexpensive. Furthermore, a variety of proteins bind specifically to carbohydrate polymers and other oligosaccharides and can be used as the source of PBP for the subject invention. As an example, fusion proteins can be prepared which include the carbohydrate polymer-binding portion of a protein which binds to a carbohydrate as a means for separating and/or purifying the fusion protein using the subject phase separation system. Thus, use of the PBP provides a generic means for affinity separation and/or purification of any polypeptide or a chemical moiety by attaching it to a PBP which can bind to a phase-forming oligosaccharide polymer. The selective binding of the PBP from the oligosaccharide polymer makes it especially suitable for the purification and/or isolation of a wide variety of compounds using a single oligosaccharide polymer phase separation system. It is unnecessary to prepare separate phase separation systems for each compound to be separated, i.e., to prepare specific polymer-ligands for each compound. Also, oligosaccharides have many binding sites as compared to other phase-separator polymers which are used, thus significantly increasing the capacity of the polymer to bind the partitioning ligand.

Use of one or more thermoseparating polymers in the two phase system offers the additional advantages of a high affinity separation to the phase containing the polymer to which the PBP binds followed by a simple method for recovering and recycling the polymer. PBP compounds bind specifically and strongly to the polymer but can be removed easily by elution with water or at high pH at ambient to physiologic temperatures, generally less than 40° C. and generally in the range of 20° C. For non-protein compounds, the PBP can be removed from the compound by proteolysis using a general protease such as protease K at 30° C., pH 7.0. The PBP thus provides a means of attaching compounds to the oligosaccharide polymer, which compounds later can be removed. Mutant PBPs or PBDs with varying affinities for the phase-forming oligosaccharide also can be obtained to vary the affinity as required for particular systems and/or applications. As desired, the PBP may comprise up to the entire polysaccharidase enzyme, including the protein having hydrolytic activity or may be essentially free of hydrolytic activity where a sequence including only the PBP is used. The latter is desirable where the integrity of the substrate is to be maintained so that it can be reused. Treatment of the polysaccharide with desorption solutions as described above does not alter the surface structure of the polysaccharide. The alternative procedure involving the use of a non-specific protease to debind the PBP conjugate from a matrix acts directly on the conjugate and does not modify the polysaccharide surface. By introducing a linkage group between the PBP and the compound of interest which is clearable by specific reagents, the compound of interest alone can be obtained leaving the PBP bound to the oligosaccharide polymer. Other key advantages of this system include that it is linearly scalable by volume from a laboratory protocol to a commercial protocol and that the system can be run as a continuous process.

Novel polypeptide compositions can include those having the following formula:

$$PBP-MR-X \quad (1)$$

wherein:

PBD is characterized as a consecutive sequence of amino acids from the substrate binding region of a polysaccharidase or other protein which binds to a polysaccharide substrate to provide for high affinity binding to a substrate of the polysaccharidase and, optionally, essentially lacking in polysaccharidase activity. The PBP is at least as large as the minimum number of amino acids in a sequence required to bind a polysaccharide and for use in a phase separation system, further is characterized as capable of binding to a phase forming oligosaccharide;

MR is the middle region, and can be a bond; short linking group of from 2 to 30 carbon atoms, or have from about 2 to about 20 amino acids. The region can include an amino acid sequence providing for specific cleavage of the fusion protein, usually a sequence corresponding to that recognized by a proteolytic enzyme of high specificity such as an IgA1 protease or Factor Xa; and X can be any peptide of interest or a chemical moiety. X is characterized as having up to the entire sequence of a polypeptide of interest, and can be an enzyme, a hormone, an immunoglobulin, peptide, etc.

Novel polypeptide compositions include those having the following formula:

$$PBP-Z \text{ or} \quad (2)$$

$$PBP-MR-Z \quad (3)$$

wherein:

PBP and MR are defined as above; and Z is a chemical moiety that is attached to the PBP. Z indicates only the moiety, not the stoichiometry of the moiety. The stoichiometry can be variable.

The PBP can be obtained from a variety of sources, including enzymes which bind to oligosaccharides which find use in the subject invention. Two types of oligosaccharides find use in the subject invention, (1) the oligosaccharide in the phase separation system, and (2) the oligosaccharide used in the solid phase system, such as is used for removal of a cleavage enzyme. The phase separation system oligosaccharide generally has the characteristics of being soluble in an aqueous solution, having high affinity for and capacity to bind to the composition comprising the PBP and compound of interest capable of phase-separation such that compound comprising the polysaccharide binding peptide is highly enriched in one of the phases, generally ≧ about 70%, preferably ≧ about 80%. In Table 1 below, is a partial list of oligosaccharides known to form aqueous two-phase systems with either another polymer or a strong electrolyte.

TABLE 1

Phase-Forming Oligosaccharides

| Uncharged Polysaccharides[1] Compounds | Charged Polysaccharides | Low Molecular Weight |
|---|---|---|
| Dextran | Na carboxymethyl dextran | Dextrins derived from cellulose (Cellotriose, cellotetraose, etc.) |
| Hydroxypropyl dextran | Na carboxymethyl cellulose | Xylose, xylobiose, xylotriose, etc. |
| Carboxymethyl dextran | Na dextran sulfate | Maltodextrins and derivatives |
| Maltodextrin | DEAE dextran | |
| Arabinogalactan | Polygalacturonic acid (pectin) | |
| Hydroxypropyl starch | | |
| Amylopectin | | |
| Methyl cellulose | | |
| Hydroxyethyl cellulose | | |
| Ethylhydroxyethyl cellulose | | |
| Carboxymethyl cellulose | | |
| Hydroxypropyl cellulose | | |
| Ficoll | | |
| Carboxymethyl starch | | |
| Hydroxyethyl starch | | |
| Pullulan | | |

[1]Polymers can be crude or purified.

Other polysaccharides which are likely to form two-phase systems include: mixtures of low-molecular weight cellosaccharides; chitosan and other chitin derivatives; all water-soluble glucans (α, β, and/or mixed linkage with degree of polymerization>3), modified glucans, and/or derivatized glucans; cereal β-glucans such as barley or oat β-glucans; and mannans, glucommannans, galactomannans, xyloglucans.

Another group of polysaccharide polymers which form two-phase systems include water-soluble amphipolar polymers which are thermoseparating in water. When a binary aqueous solution of the polymer is heated above its cloud point temperature (CPT), the solution phase separates into two macroscopic phases. One of the phases, usually the bottom phase is heavily enriched with polymer, while the other phase typically contains little to no polymer. Polysaccharide-based polymers which are known to exhibit thermoseparating properties include methyl cellulose, ethyl hydroxyethyl cellulose, propyl hydroxyethyl cellulose, and hydroxypropyl methyl cellulose. However, essentially any water-soluble β-1,4-linked cellosaccharide should show thermoseparating properties. Johansson, et al. (1993). *Macromolecules*, 26, 4478; Harris, et al. (1991). *Bioseparations* 2, 237; Alfred P. A. et al. (1992). *Bioseparations*, 2, 363; and Alfred P. A. et al. (1994). *J. Chromatog.*, 659, 289. Other water soluble polymers which thermoseparate include polyethylene glycol, polyethylene oxide, polypropylene glycol and linear random copolymers of ethylene oxide and propylene oxide (trade names UCON and Pluronic).

For the solid phase recovery systems, a variety of polysaccharide substrates are of interest. These include cellulose, a polysaccharide composed of D-glucopyranose units joined by β-1,4-glycosidic linkages and its esters, e.g., cellulose acetate; xylan, in which the repeating backbone unit is β-1,4-D-xylopyranose; chitin, which resembles cellulose in that it is composed of β-1,4-linked N-acetyl, 2-amino-2-deoxy-β-D-glucopyranose units. Enzymes that are capable of binding to polysaccharides, such as those listed above, are of interest in the subject invention as a source of amino acid sequences capable of binding to such substrates.

In Table 6 below are listed those binding domains which bind to one or more soluble/insoluble polysaccharides including all binding domains with affinity for soluble glucans (α, β, and/or mixed linkages). The N1 cellulose-binding domain from endoglucanase CenC of *C. fimi* is the only protein known to bind soluble cellosaccharides and one of a small set of proteins which are known to bind any soluble polysaccharides. Also, listed in Tables 2 to 5 are examples of proteins containing putative β-1,3-glucan-binding domains (Table 2); proteins containing Streptococcal glucan-binding repeats (Cpl superfamily) (Table 3); enzymes with chitin-binding domains (Table 4), and starch-binding domains (Table 5).

TABLE 2

Overview of proteins containing putative β-1,3 glucan-binding domains

| Source (strain)[1] | Protein | accession N° | Ref[2] |
|---|---|---|---|
| Type I | | | |
| B. circulans (WL-12) | GLCA1 | P23903/M34503/ JQ0420 | 1 |
| B. circulans (IAM 1165) | BglH | JN0772/D17519/ S67033 | 2 |

TABLE 2-continued

Overview of proteins containing putative β-1,3 glucan-binding domains

| Source (strain)[1] | Protein | accession N° | Ref[2] |
|---|---|---|---|
| Type II | | | |
| Actinomadura sp. (FC7) | | XynII | U08894 3 |
| Arthrobacter sp. (YCWD3) | | GLCI | D23668 9 |
| O. xanthineolytica | GLC | P22222/M60826/ A39094 | 4 |
| R. faecitabidus (YLM-50) | | RP I Q05308/A45053/ D10753 | 5 a,b |
| R. communis | Ricin | A12892 | 6 |
| S. lividans (1326) | XlnA | P26514/M64551/ JS07986 | 7 |
| T. tridentatus | FactorGa | D16622 | 8 |

[1]B.: Bacillus, O.: Oerskovia, R. faecitabidus: Rarobacter faecitabidus, R. communis: Ricinus communis, S.: Streptomyces, T: Tachypleus (Horseshoe Crab)
[2]References
1) Yahata et al. (1990) Gene 86, 113–117; 2) Yamamoto et al. (1993) Biosci. Biotechnol. Biochem. 57, 1518–1525; 3) Harpin et al. (1994) EMBL Data Library; 4) Shen et al. (1991) J. Biol. Chem. 266, 1058–1063 5a) Shimoi et al. (1992) J. Biol. Chem. 267, 25189–25195; 5b) Shimoi et al. (1992) J. Biochem 110, 608–613; 6) Horn et al. (1989) Patent A12892; 7) Shareck et al. (1991) Gene 107, 75–82; 8) Saeki et al. (1994) J. Biol. Chem. 269, 1370–1374; 9) Watanabe et al. (1993) EMBL Data Library

TABLE 3

Overview of proteins containing Streptococcal glucan-binding repeats (Cpl superfamily)

| Source | Protein | Accession N° | Ref.[1] |
|---|---|---|---|
| S. downei (sobrinus) (0MZ176) | GTF-I | D13858 | 1 |
| S. downei (sobrinus) (MFe28) | GTF-I | P11001/M17391 | 2 |
| S. downei (sobrinus) (MFe28) | GTF-S | P29336/M30943/A41483 | 3 |
| S. downei (sobrinus) (6715) | GTF-I | P27470/D90216/A38175 | 4 |
| S. downei (sobrinus) | DEI | L34406 | 5 |
| S. mutants (Ingbritt) | GBP | M30945/A37184 | 6 |
| S. mutants (GS-5) | GTF-B | A33128 | 7 |
| S. mutants (GS-5) | GTF-B | P08987/M17361/B33135 | 8 |
| S. mutants | GTF-B[3'-ORF] | P05427/C33135 | 8 |
| S. mutants (GS-5) | GTF-C | P13470/M17361/M22054 | 9 |
| S. mutants (GS-5) | GTF-C | not available | 10 |
| S. mutants (GS-5) | GTF-D | M29296/A45866 | 11 |
| S. salivarius | GTF-J | A44811/S22726/S28809 Z11873/M64111 | 12 |
| S. salivarius | GTF-K | S22737/S22727/Z11872 | 13 |
| S. salivarius (ATCC 25975) | GTF-L | L35495 | 14 |
| S. salivarius (ATCC 25975) | GTF-M | L35928 | 14 |
| S. pneumoniae R6 | LytA | P06653/A25634/M13812 | 15 |
| S. pneumoniae | PspA | A41971/M74122 | 16 |
| Phage HB-3 | HBL | P32762/M34652 | 17 |
| Phage Cp-1 | CPL-1 | P15057/J03586/A31086 | 18 |
| Phage Cp-9 | CPL-9 | P19386/M34780/JQ0438 | 19 |
| Phage EJ-1 | EJL | A42936 | 20 |
| C. difficile (VPI 10463) | ToxA | P16154/A37052/M30307 X51797/S08638 | 21 |
| C. difficile (BARTS W1) | ToxA | A60991/X17194 | 22 |
| C. difficile (VPI 10463) | ToxB | P18177/X53138/X60984 S10317 | 23, 24 |
| C. difficile (1470) | ToxB | S44271/Z23277 | 25, 26 |
| C. novyi | a-toxin | S44272/Z23280 | 27 |
| C. novyi | a-toxin | Z48636 | 28 |
| C. acetobutylicum (NCIB8052) | CspA | S49255/Z37723 | 29 |

TABLE 3-continued

Overview of proteins containing Streptococcal glucan-binding repeats (Cpl superfamily)

| Source | Protein | Accession N° | Ref.[1] |
|---|---|---|---|
| C. acetobutylicum (NCIB8052) | CspB | 30 | Z50008 |
| C. acetobutylicum (NCIB8052) | CspC | 30 | Z50033 |
| C. acetobutylicum (NCIB8052) | CspD | 30 | Z50009 |

[3]References
1) Sato et al (1993) DNA sequence 4, 19–27; 2) Ferreti et al. (1987) J. Bacteriol. 169, 4271–4278; 3) Gilmore et al. (1990) J. Infect. Immun. 58, 2452–2458; 4) Abo et al. (1991) J. Bacteriol. 173, 989–996; 5) Sun et al. (1994) J. Bacteriol. 176, 7213–7222; 6) Banas et al. (1990) J. Infect. Immun. 58, 667–673; 7) Shiroza et al.(1990) Protein Sequence Database; 8) Shiroza et al. (1987) J. Bacteriol. 169, 4263–4270; 9) Ueda et al. (1988) Gene 69, 101–109; 10) Russel (1990) Arch. Oral. Biol. 35, 53–58; 11) Honda et al. (1990) J. Gen. Microbiol. 136, 2099–2105; 12) Giffard et al.(1991) J. Gen. Microbiol. 137, 2577–2593; 13) Jacques (1992) EMBL Data Library; 14) Simpson et al. (1995) J. Infect. Immun. 63, 609–621; 15) Gargia et al. (1986) Gene 43, 265–272; 16) Yother et al. (1992) J. Bacteriol. 174, 601–609; 17) Romero et al. (1990) J. Bacteriol. 172, 5064–5070; 18) Garcia et al. (1988) Proc. Natl. Acad. Sci, USA 85, 914–918; 19) Garcia et al. (1990) Gene 86, 81–88; 20) Diaz et al.(1992) J. Bacteriol. 174, 5516–5525; 21) Dove et al. (1990) J. Infect. Immun. 58, 480–488; 22) Wren et al. (1990) FEMS Microbiol. Lett. 70, 1–6; 23) Barroso et al. (1990) Nucleic Acids Res. 18, 4004–4004 24) von Eichel-Streiber et al. (1992) Mol. Gen. Genet. 233, 260–268; 25) Sartinger et. al. (1993) EMBL Data Library; 26) von Eichel-Streiber et al. (1995) Mol. Microbiol. In Press; 27) Hoffmann et al. (1993) EMBL Data Library; 28) Hofmann et al. (1995) Mol. Gen. Genet. In Press; 29) Sanchez et al. (1994) EMBL Data Library; 30) Sanchez et al. (1995) EMBL Data Library

TABLE 4

Overview of Enzymes with Chitin-binding Domains

| Source (strain) | Enzyme | Accession N° | Ref.[2] |
|---|---|---|---|
| Bacterial.enzymes | | | |
| Type I | | | |
| Aeromonas sp. (No10S-24) | Chi | D31818 | 1 |
| Bacillus circulans (WL-12) | ChiA1 | P20533/M57601/A38368 | 2 |
| Bacillus circulans (WL-12) | ChiD | P27050/D10594 | 3 |
| Janthinobacterium lividum | Chi69 | U07025 | 4 |
| Streptomyces griseus | Protease C | A53669 | 5 |
| Type II | | | |
| Aeromonas cavia (K1) | Chi | U09139 | 6 |
| Alteromonas sp (0–7) | Chi85 | A40633/P32823/D13762 | 7 |
| Autographa californica (C6) | NPH-128[a] | P41684/L22858 | 8 |
| Serratia marcescens | ChiA | A25090/X03657/L01455/P07254 | 9 |
| Type III | | | |
| Rhizopus oligosporus (IFO8631) | Chi1 | P29026/A47022/D10157/S27418 | 10 |
| Rhizopus oligosporus (IFO8631) | Chi2 | P29027/B47022/D10158/S27419 | 10 |
| Saccharomyces cerevisiae | Chi | S50371/U17243 | 11 |
| Saccharomyces cerevisiae (DBY939) | Chi1 | P29028/M74069 | 12 |
| Saccharomyces cerevisiae (DBY918) | Chi2 | P29029/M7407/B41035 | 12 |

| Source (strain) | Enzyme | Accession N° | Ref.[4] |
|---|---|---|---|
| Plant enzymes | | | |
| Hevein superfamily | | | |
| Allium sativum | Chi | M94105 | 13 |
| Amaranthus caudatus | AMP-1[b] | P27275/A40240 | 14, 15 |
| Amaranthus caudatus | AMP-2[b] | S37381/A40240 | 14, 15 |
| Arabidopsis thaliana (CV. colombia) | ChiB | P19171/M38240/B45511 | 16 |
| Arabidopsis thaliana | PHP[c] | U01880 | 17 |
| Brassica napus | Chi | U21848 | 18 |
| Brassica napus | Chi2 | Q09023/M95835 | 19 |
| Hevea brasiliensis | Hev1[d] | P02877/M36986/A03770/A38288 | 20, 21 |
| Hordeum vulgare | Chi33 | L34211 | 22 |
| Lycopersicon esculentum | Chi9 | Q05538/Z15140/S37344 | 23 |
| Nicotiana tabacum | CBP20[e] | S72424 | 24 |
| Nicotiana tabacum | Chi | A21091 | 25 |
| Nicotiana tabacum (cv. Havana) | Chi | A29074/M15173/S20981/S19855 | 26 |
| Nicotiana tabacum (FB7-1) | Chi | JQ0993/S0828 | 27 |

TABLE 4-continued

Overview of Enzymes with Chitin-binding Domains

| Source (strain) | Enzyme | Accession N° | Ref.[1] |
|---|---|---|---|
| Nicotiana tabacum (cv. Samsun) | Chi | A16119 | 28 |
| Nicotiana tabacum (cv. Havana) | Chi | P08252/X16939/S08627 | 27 |
| Nicotiana tabacum (cv. BY4) | Chi | P24091/X51599/X64519//S13322 | 26, 27, 29 |
| Nicotiana tabacum (cv. Havana) | Chi | P29059/X64518/S20982 | 26 |
| Oryza sativum (IR36) | ChiA | L37289 | 30 |
| Oryza sativum | ChiB | JC2253/S42829/Z29962 | 31 |
| Oryza sativum | Chi | S39979/S40414/X56787 | 32 |
| Oryza sativum (cv. Japonicum) | Chi | X56063 | 33 |
| Oryza sativum (cv. Japonicum) | Chi1 | P24626/X54367/S14948 | 34 |
| Oryza sativum | Chi2 | P25765/S15997 | 35 |
| Oryza sativum (cv. Japonicum) | Chi3 | D16223 | 32 |
| Oryza sativum | ChiA | JC2252/S42828 | 30 |
| Oryza sativum | Chi1 | D16221 | 32 |
| Oryza sativum (IR58) | Chi | U02286 | 36 |
| Oryza sativum | Chi | X87109 | 37 |

| Source (strain) | Enzyme | Accession N° | Ref.[1] |
|---|---|---|---|
| Pisum sativum (cv. Birte) | Chi | P36907/X63899 | 38 |
| Pisum sativum (cv. Alcan) | Chi2 | L37876 | 39 |
| Populus trichocarpa | Chi | S18750/S18751/X59995/P29032 | 40 |
| Populus trichocarpa (H11-11) | Chi | U01660 | 41 |
| Phaseolus vulgaris (cv. Saxa) | Chi | A24215/S43926/Jq0965/P36361 | 42 |
| Phaseolus vulgaris (cv. Saxa) | Chi | P06215/M13968/M19052/A25898 | 43, 44, 45 |
| Sambucus nigra | PR-3[f] | Z46948 | 46 |
| Secale cereale | Chi | JC2071 | 47 |
| Solanum tuberosum | ChiB1 | U02605 | 48 |
| Solanum tuberosum | ChiB2 | U02606 | 48 |
| Solanum tuberosum | ChiB3 | U02607/S43317 | 48 |
| Solanum tuberosum | ChiB4 | U02608 | 48 |
| Solanum tuberosum (cv. Maris Piper) | WIN-1[g] | P09761/X13497/S04926 | 49 |
| Solanum tuberosum (cv. Maris Piper) | WIN-2[g] | P09762/X13497/S04927 | 49 |
| Triticum aestivum | Chi | S38670/X76041 | 50 |
| Triticum aestivum | WGA-1[b] | P10968/M25536/S09623/S07289 | 51, 52 |
| Triticum aestivum | WGA-2[h] | P02876/M25537/S09624 | 51, 53 |
| Triticum aestivum | WGA-3[h] | P10969/J02961/S10045/A28401 | 54 |
| Ulmus americana (NPS3-487) | Chi | L22032 | 55 |
| Urtica dioica | AGL[i] | M87302 | 56 |
| Vigna unguiculata (cv. Red caloona) | Chi1 | X88800 | 57 |

[1]NHP: nuclear polyhedrosis virus endochitinase like sequence
Chi: chitinase
[b]anti-microbial.peptide,
[c]pre-hevein like protein,
[d]hevein,
[e]chitin-binding protein,
[f]patogenesis related protein,
[g]wound-induced protein,
[h]wheat germ agglutinin,
[i]agglutinin (lectin)
[1]References Chitin-binding domains
1) Udea et al. (1994) J. Ferment. Bioeng. 78, 205–211; 2) Watanabe et al. (1990) J. Biol. Chem. 265, 15659–16565; 3) Watanabe et al. (1992) J. Bacteriol. 174, 408–414; 4) Gleave et al. (1994) EMBL Data Library; 5) Sidhu et al. (1994) J. Biol. Chem. 269, 20167–20171; 6) Jones et al. (1986) EMBO J. 5, 467–473; 7) Sitrit et al. (1994) EMBL Data Library;
8) Genbank entry only; 9) Tsujibo et al. (1993) J. Bacteriol. 175, 176–181; 10) Yanai et al. (1992) J. Bacteriol. 174, 7398–7406; 11 22, 1187–1190; 16) Samac et al. (1990) Plant Physiol. 93, 907–914; 17) Potter et al. (1993) Mol. Plant Microbe Interact. 6, 680–685; 18) Buchanan-Wollaston (1995) EMBL Data Library;
19) Hamel et al. (1993) Plant Physiol. 101, 1403–1403; 20) Broekaert et al. (1990) Proc. Natl. Acad. Sci. USA 87, 7633–7637; 21) Lee et al. (1991) J. Biol. Chem. 266, 15944–15948; 22) Leah et al. (1994) Plant Physiol. 6, 579–589; 23) Danhash et al. (1993) Plant Mol. Biol. 22 1017–1029; 24) Ponstein et al. (1994) Plant Physiol. 104, 109–118;
25) Meins et al. (1991) Patent EP0418695-A1; 26) van Buuren et al. (1992) Mol. Gen. Genet. 232, 460–469; 27) Shinshi et al. (1990) Plant Mol 226, 289–296; 36) Muthukrishhnan et al. (1993) EMBL Data Library; 37) Xu (1995) EMBL Data Library; 38) Vad et al. (1993) Plant Sci 92, 69–79; 39) Chang et al. (1994) EMBL Data Library;
40) Davis et al. (1991) Plant Mol. Biol. 17, 631–639; 41) Clarke et al. (1994) Plant Mol. Biol. 25, 799–815; 42) Broglie et al. (1989) Plant Cell 1, 599–607; 43) Broglie et al. (1986) Proc. Natl. acad. Sci. USA 83, 6820–6824; 44) Lucas et al. (1985) FEBS Lett. 193, 208–210; 45) Hedrick et al. (1988) Plant Physiol. 86, 182–186;
46) Roberts et al. (1994) EMBL Data LibraryI; 47) Vamagami et al. (1994) Biosci. Biotechnol. Biochem. 58, 322–329; 48) Beerhues et al. (1994) Plant Mol. Biol. 24, 353–367; 49) Stanford et al. (1989) Mol. Gen. Genet. 215, 200–208; 50) Liao et al. (1993) EMBL Data Library; 51) Smith et al. (1989) Plant Mol. Biol. 13, 601–603;

TABLE 4-continued

Overview of Enzymes with Chitin-binding Domains

52) Wright et al. (1989) J. Mol. Evol. 28, 327–336; 53) Wright et al. (1984) Biochemistry 23, 280–287; 54) Raikhel et al. (1987) Proc. Natl. acad. Sci. USA 84, 67 et al. (1992) J. Biol. Chem. 267, 11085–11091 57) Vo et al. (1995) EMBL Data Library

TABLE 5

Overview of Enzymes Containing Starch-binding Domains

| Source (strain) | Enzyme | Accession N° | Ref.[5] |
|---|---|---|---|
| A. awarori (var. kawachi) | AMYG | P23176/D00427/JT0479 | 1, 2 |
| A. niger (T21) | AMYG | 573370 | 3 |
| A. niger -A. awamori | AMYG1/G2 | P04064/A90986/A29166/X00712/X00548 K02465 | 4, 5, 6 7, 8, 9 |
| A. oryzae | AMYG (GLAA) | P36914/JQ1346/D01035/S75274/DO1108 | 10, 11 |
| A. Shirousamii | AMYG (GLA) | P22832/JQ0607/D10460 | 12 |
| Bacillus sp. (B1018) | AMY[a] | P17692/M33302/D90112/S09196 | 13 |
| Bacillus sp. (TS-23) | a-AMY | U22045 | 14 |
| Bacillus sp. (1-1) | CGT | P31746/S26399 | 15 |
| Bacillus sp. (6.63) | CGT | P31747/X66106/S21532 | 16 |
| Bacillus sp. (17-1) | CGT | P30921/M28053/A37208 | 17 |
| Bacillus sp. (38-2) | CGT | P09121/M19880/D00129/S24193 | 18, 19 |
| Bacillus sp. (1011) | CGT | P05618/A26678/M17366 | 20 |
| Bacillus sp. (DSM5850) | CGT | A18991 | 21 |
| Bacillus sp. (KC 201) | CGT | D13068 | 15, 22 |
| B. cereus (SPOII) | b-AMY | A48961/P36924/S54911 | 23 |
| B. circulans (8) | CGT | P30920/X68326/S23674 | 24 |
| B. circulans (251) | CGT | X78145 | 25 |
| B. Licheriformis | CGTA | P14014/X15752/515920 | 26 |
| B. macerans (IFO 3490) | CGTM (CDG1) | P04830/X5904/S31281 | 27 |
| B. macerans (IAM 1243) | CGT | M12777 | 28 |
| B. macerans | CGT (CDG2) | P31835/S26589 | 29 |
| B. ohbensis | CGT | P27036/D90243 | 30 |
| B. stearothermophilus | AMYM[b] | P19531/M36539/S28784 | 31 |
| B. stearothermophilus (NO2) | CGT | P31797/X59042/S26588/X59043/X59404/S31284 | 32 |
| C. rolfsii (AHU 9627) | AMYG2 | D49448 | 33 |
| D. discoideum | ORF | S15693/X51947 | 34 |
| Source | Enzyme | Accession N° | Ref.[5] |
| H. grisea (var. thermoidea) | GLA1 | M89475 | 35 |
| H. resinae (ATCC 20495) | GAMP | Q03045/X68143/X67708/S31422/S33908 | 36–38 |
| K. pneumoniae (M5A1) | CGT | P08704/M15264/A29023 | 39 |
| N. crassa (74-OR23-1A) | GLA-1 | P14804/X67291/S13711/S13710/S36364 | 40, 41 |
| P. saccharophila (IAM1504) | MTA[c] | P22963/X16732/505667 | 42 |
| Pseudomonas sp. (KO-8940) | AMF-1[d] | D10769/JS0631/D01143 | 43 |
| P. stutzeri (MO-19) | AMYP[c] | P13507/M24516/A32803 | 44 |
| S. griseus (IMRU 3570) | AMY | P30270/X57568/S14063 | 45 |
| S. limosus (S. albidoflavus) | AML | P09794/M18244/B28391 | 46 |
| S. violaceus (S. venezuela) (ATCC 15068) | AML | P22998/M25263/JS0101 | 47 |
| Th. curvata (CCM 3352) | TAM[e] | P29750/X59159/JH0638 | 48 |
| Th. thermosulfurogenes (DSM3896/EM1)[f] | AMYA | P26827/X54654/X54982/S17298/S37706 | 49 |
| Th. thermosulfurogenes (ATCC 33743) | AMYB | P19584/M22471/A31389 | 50 |

[a]Raw-starch digesting amylase,
[b]Maltogenic a-amylase,
[c]Maltotetraose-forming amylase (1,4-a-maltotetrahydrolase,
[d]Maltopentaose-forming amylase,
[e]thermostable a-amylase,
[f]formerly Clostridium thermosulfurogenes.
AMYG, GAM and GLA: glucoamylase, AMY or AML: alpha-amylase, CGT: β-cyclodextrin glycosyltransferase or cyclomaltodextrin glucanotransferase, ORF: open reading frame
A.: Aspergillus, B.: Bacillus, C.: Corticium, D.: Dictiostelium, H. grisea: Humicola grisea, H. resinea: Hormoconis resinae (Amorphotheca resinae), K.: Klebsiella, N.: Neurospora, S.: Streptomyces, Th. curvata: Thermomonospora curvata, Th. Thermoanaerobacter.
[5]References Starch-binding Domains
1) Hayashida et al. (1989) Agric. Biol. Chem. 53, 135–141; 2) Hayashida et al. (1989) Agric. Biol. Chem. 53, 923–929; 3) Zhong et al. (1994) Wei Sheng Wu Hseuh Pao 34, 184–190; 4) Boel et al. (1984) EMBO J. 3, 1097–1102; 5) Boel et al. (1984) EMBO J. 3, 1581–1583; 6) Svensson et al. (1986) Eur. J. Biochem. 154, 497–502; 7) Svensson et al. (1983) Carlsberg Res. Commun.. 48, 529–544; 8) Nunberg et al. (1984) Mol. Cell. Biol. 4, 2306–2315; 9) Flwer et al. (1990) Curr. Genet. 18, 5 Huber, O. and Szejtli, J. Eds. pp 71–76. Kluwer, Academic Publishers; 16) Akhmetzjanov (1992) EMBL Data Library; 17) Kaneko et al. (1989) J. Gen. Microbiol. 135, 3447–3457; 18) Kaneko et al. (1988) J. Gen. Microbiol. 134, 97–105;

TABLE 5-continued

Overview of Enzymes Containing Starch-binding Domains

19) Hamamoto et al. (1987) Agric. Biol. Chem. 51, 2019–2022; 20) Kimura et al. (1987) J. Bacterio 623–627; 24) Nitschke et al. (1990) Appl. Microbial. Biotechnol. 33, 542–546; 25) Lawson et al. (1994) J. Mol. Biol. 236, 590–560; 26) Hill et al. (1990) Nucleids Acids Res. 18, 199–199; 27) Fujiwara et al.(1992) Appl. Environ. Microbiol. 58, 4016–4025;
28) Takano et al. (1986) J. Bacteriol. 166, 1118–1122; 29) Sugimoto et al. Patent N° UK2169902; 30) Sin et al. (1991) Appl. Microbiol. Biotechnol. 35, 600–605; 31) Didericksen et al. (1988) FEMS Microbiol. Lett. 56, 53–60; 32) Fujiwara et al. (1992) Appl. Environ. Microbiol. 58, 4016–4025; 33) Nagasaka et al. (1995) EMBL Data Library;
34) Maniak et al.(1990) Nucleic Acids Res. 18, 3211–3217; 35) Berka et al. (1992) EMBL Data Library; 36) Joutsjoki et al. (1992) FEMS Microbiol. Lett. 78, 237–244; 37) Vainio et al. (1993) Curr. Genet, 24, 38–44; 38) Fagerstrom et al. (1990) J. Gen. Microbiol. 136, 913–920; 39) Binder et al. (1986) Gene 47, 269–277;
40) Stone et al. (1989) Curr. Genet. 24, 205–211 41) Koh-Laur et al. (1989) Enzym. Microb. Technol. 11, 692–695; 42) Zhoe et al. (1989) FEBS Lett, 255, 37–41; 43) Shida et al. (1991) Biosci. Biotechnol. Biochem. 56, 76–80; 44) Fujita et al. (1989) J. Bacteriol. 171, 1333–1339; 45) Vigal et al. (1991) Mol. Gen. Genet. 225, 278–288; 46) Long et al. (1987) J. Bacteriol. 169, 5745–5754;
47) Virolle et al. (1988) Gene 74, 321–334; 48) Petricek et al. (1992) Gene 112, 77–83; 49) Bahl et al. (1991) Appl. Environ. Microbiol. 57, 1554–1559; 50) Kitamoto et al. (1988) J. Bacteriol. 170, 5848–5854

New PBPs with interesting binding characteristics and specificities can be identified and screened for in a variety of ways using various different experimental approaches and methodologies. These include spectroscopic (titration) methods such as: NMR spectoscopy (Zhu et al. *Biochemistry* (1995) 34:, Gehring et al. *Biochemistry* (1991) 30:5524–5531), UV difference spectroscopy (Belshaw et al. *Eur. J. Biochem.* (1993) 211:717–724), fluorescence (titration) spectroscopy (Miller et al. *J. Biol. Chem.* (1983) 258:13665–13672), UV or fluorescence stopped flow analysis (De Boeck et al. *Eur. J. Biochem.* (1985) 149:141–415), affinity methods such as affinity electrophoresis (Mimura et al. *J. chromatography* (1992) 597:345–350) or affinity chromatography on immobilized mono or oligosaccharides, precipitation or agglutination analysis including turbidimetric or nephelometric analysis (Knibbs et al. *J. Biol. Chem.* (1993) 14940–14947), competitive inhibition assays (with or without quantitative IC50 determination) and various physical or physico-chemical methods including differential scanning or isothermal titration calorimetry (Sigurskjold et al. *J. Biol. Chem.* (1992) 267:8371–8376; Sigurskjold et al. *Eur. J. Biol.* (1994) 225:133–141) or comparitive protein stability assays (melts) in the absence or presence of oligo saccharides using thermal CD or fluorescence spectroscopy. Both qualitative and quantitative (association or dissociation constants, IC50 values, thermodynamic parameters, etc.,) analysis can be performed with these methods. Identification of PBPs with both higher and lower binding affinities for soluble oligosaccharides polymers are of interest; depending upon a particular application, a lower rather than a higher binding affinity can be useful, for example to improve facility of removal of the oligosaccharide polymer following partitioning and/or isolation of the oligosaccharide polymer phase enriched in the compound comprising the PBP.

TABLE 6

Sources of Polysaccharide Binding Domains

| Binding Domain | Proteins Where Binding Domain is Found |
|---|---|
| Cellulose Binding Domains[1] | β-glucanases (avicelases, CMCases, cellodextrinases) exoglucanses or cellobiohydrolases cellulose binding proteins xylanases mixed xylanases/glucanases |

TABLE 6-continued

Sources of Polysaccharide Binding Domains

| Binding Domain | Proteins Where Binding Domain is Found |
|---|---|
| | esterases chitinases β-1, 3-glucanases β-1, 3-(β-1, 4)-glucanases (β-)mannanases β-glucosidases/galactosidases cellulose synthases (unconfirmed) |
| Starch/Maltodextrin Binding Domains | α-amylases[2, 3] β-amylases[4, 5] pullulanases glucoamylases[6, 7] cyclodextrin glucotransferases[8–10] (cyclomaltodextrin glucanotransferases) maltodextrin binding proteins[11] |
| Dextran Binding Domains | (Streptococcal) glycosyl transferases[12] dextran sucrases (unconfirmed) Clostridial toxins[13, 14] glucoamylases[6] dextran binding proteins |
| β-Glucan Binding Domains | β-1, 3-glucanases[15, 16] β-1, 3-(β-1, 4)-glucanases (unconfirmed) β-1, 3-glucan binding protein[17] |
| Chitin Binding Domains | chitinases chitobiases chitin binding proteins (see also cellulose binding domains) Heivein |

[1]Gilkes et al, Adv. Microbiol Reviews, (1991) 303–315;
[2]Sogaard et al., J. Biol. Chem. (1993) 268:22480;
[3]Weselake et al., Cereal Chem. (1983) 60:98;
[4]Svensson et al., J. (1989) 264:309;
[5]Jespersen et al., J. (1991) 280:51;
[6]Belshaw et al., Eur. J. Biochem. (1993) 211:717;
[7]Sigurskjold et al., Eur. J. Biochem. (1994) 225:133;
[8]Villette et al, Biotechnol Appl. Biochem. (1992) 16:57;
[9]Fukada et al., Biosci. Biotechnol. Biochem. (1992) 56:556;
[10]Lawson et al., J. Mol. Biol. (1994) 236:590.
[11]Sharff et al., Biochemistry (1992) 31:10657;
[12]Lis et al., Appl. Environ. Microbiol. (1995) 61:2040;
[13]von Eichel-Streiber et al., J. Bacteriol. (1992) 174:6707;
[14]von Eichel-Streiber et al., Mol. Gen. Genet. (1992) 233:260.
[15]Klebl et al., J. Bacteriol. (1989) 171:6259;
[16]Watanabe et al., J. Bacteriol. (1992) 174:186;
[17]Duvic et al., J. Biol. Chem. (1990) 265:9327.

The PBP can be obtained following isolation and purification of the enzyme by clipping off the PBP from the remainder of the enzyme. For use in the phase separation system, the PBP is screened for binding to soluble phase-forming oligosaccharides. While any of a number of methods can be used for screening, including NMR alone, NMA/calorimetry, affinity electrophoresis alone, affinity electrophoresis/competition assay, and binding isotherms. Binding equilibrium studies using isothermal titration microcalorimetry (ITC) are preferred. The advantage of isothermal titration microcalorimetry (FTC) in binding equilibrium studies derives from the fact that binding isotherms are defined by the experiment in terms of heats of reaction; as such, they allow a direct estimation of enthalpy (and entropy (changes in addition to the association constant. Thus, a single microcalorimetric titration provides a complete characterization of the binding energetics along with the binding isotherm. (Haynes et al., *J. Colloid Interface Sci.*, (1994) 169:313; Colloids & Surfaces, (1994) 2:517.

Generally, for use in phase separation, the $K_a$ for binding of the PBP to soluble oligosaccharide is at least in the range of weak antibody-antigen interactions, i.e. $\geq 10^3$ M, preferably $10^4$ M, most preferably $10^6$ M. If the binding of the PBP to the oligosaccharide is exothermic or endothermic, then binding will increase or decrease, respectively, at lower temperatures, providing a means for temperature modulation of the partitioning step.

In addition to determining the oligosaccharide polymer-PBP pairing, it is also necessary to evaluate the second component of the phase separation system to be used with the oligosaccharide polymer, the phase separation means. The phase separation means can be another polymer, or a sufficient quantity of a phase inducing agent generally a strong electrolyte such as salt, usually a sulfate or citrate salt or a physical change, such as a temperature change if the cellosaccharide polymer has thermoseparating properties. Examples of polymer pairs capable of forming partition systems with comparable properties to, but lower cost than, the classic dextran/PEG system, including those based, like the dextran/PEG system, on the incompatibility between a carbohydrate and a poly(oxy-ether) are many (see Skuse et al., *Enzyme Microb. Technol.* (1992) 14:785.) Examples include, hydroxypropyl starch (Tjerneld et al., *Enzyme Microb. Technol.* (1986) 8:417), maltodextrins (Szlag et al., *ACS Symposium Series* (1990) 419:38–52), hydroxypropyl cellulose (Skuse et al., *Enzyme Microb. Technol.* (1992) 14:785), and carboxymethyl cellulose (Albertsson, *Partition of Cell Particles and Macromolecules,* Wiley Interscience (1971)) which have all been successfully used to form partition systems with PEG.

In order to develop a system, phase equilibria data are obtained for the combination of the first and second components selected, and/or inducing means using the procedure of Haynes et al. (*Fluid Phase Equilibria* (1989) 53:463) to determine the total polymer concentration, or polymer and other phase inducing agent concentration, above which a stable two-phase partition system is formed. In general, the PBP-conjugates are bound to a phase forming oligosaccharide at neutral pH in a medium ionic strength buffer of from about 10 mM to about 1 M. Binding is performed at temperatures from 4° C. to at least 70° C. depending on the components of the phase separation system. Binding is virtually instantaneous and the temperature is not critical. Once the PBP-conjugate is bound to the phase-forming oligosaccharide, it partitions into that phase.

Once the components of the phase separation system and the most appropriate polysaccharide binding moiety for a particular application have been identified, PBP can be prepared by transforming into a host cell a DNA construct comprising DNA encoding the appropriate polysaccharide binding moiety. The phrase "polysaccharide binding peptide" intends an amino acid sequence which comprises at least a functional portion of the polysaccharide binding region of a polysaccharidase or a polysaccharide binding protein. By "functional portion" is intended an amino acid sequence which binds to an oligosaccharide polymer of interest. Preferably, DNA encoding a protein of interest is ligated to the PBP DNA sequence. The fused gene encoding the composition according to formula (1), or the PBP DNA sequence alone, is expressed in a host cell, either an eukaryotic or a prokaryotic cell. Where the PBP alone has been prepared, if desired, the expressed and isolated polysaccharide binding peptide can be conjugated to a compound of interest, i.e., a protein or a chemical moiety.

The techniques used in isolating polysaccharidase genes, such as a cellulase gene, and genes for polysaccharide binding proteins are known in the art, including synthesis, isolation from genomic DNA, preparation from cDNA, or combinations thereof. (See, U.S. Pat. Nos. 5,137,819, 5,202, 247, and 5,340,731.) The sequences for several polypeptide binding domains, which bind to soluble oligosaccharides are known. (See, FIG. 1.) The DNAs coding for a variety of polysaccharidases and polysaccharide binding proteins also are known. Various techniques for manipulation of genes are well known, and include restriction, digestion, resection, ligation, in vitro mutagenesis, primer repair, employing linkers and adapters, and the like (see Sambrook et al., *Molecular Cloning, A Laboratory Manual,* Cold Spring Harbor Laboratory, Cold Spring Harbor, New York, 1989).

Generally, the method for obtaining the desired DNA comprises preparing a genomic library from an organism expressing a polysaccharidase or polysaccharide binding protein with the desired characteristics. The genome of the donor microorganism is isolated and cleaved by an appropriate restriction enzyme, such as BamHI. The fragments obtained are joined to a vector molecule which has previously been cleaved by a compatible restriction enzyme. An example of a suitable vector is plasmid pBR322 which can be cleaved by the restriction endonuclease BamHI.

The amino acid sequence of a polysaccharidase also can be used to design a probe to screen a cDNA or a genomic library prepared from mRNA or DNA from cells of interest as donor cells for a polysaccharidase gene or a polypeptide-binding protein gene. By using the polysaccharidase cDNA or binding protein cDNA or a fragment thereof as a hybridization probe, structurally related genes found in other microorganisms can be easily cloned. Particularly contemplated is the isolation of genes from organisms that express polysaccharidase activity using oligonucleotide probes based on the nucleotide sequences of genes obtainable from an organism wherein the catalytic and binding domains of the polysaccharidase are discrete, although other polysaccharide binding proteins also can be used (see, for example, Shoseyev, et al., *Proc. Nat'l. Acad. Sci.* (USA) (1992) 89:3483–3487).

Probes developed using consensus sequences for the binding domain of a polysaccharidase or polysaccharide-binding protein are of particular interest. The β-1,4-glycanases from *C. fimi* characterized to date are endoglucanases A, B, C and D (CenA, CenB, CenC and CenD, respectively), exocellobiohydrolases A and B (CbhA and CbhB, respectively), and xylanases A and D (Cex and XylD, respectively) (see Wong et al. (1986) *Gene,* 44:315; Meinke et al. (1991) *J. Bacteriol.,* 173:308; Coutinho et al., (1991) *Mol. Microbiol.* 5:1221; Meinke et al., (1993) *Bacteriol.,* 175:1910; Meinke et al., (1994) *Mol. Microbiol.,* 12:413; Shen et al., *Biochem. J.,* in press; O'Neill et al., (1986) *Gene,* 44:325; and Millward-Sadler et al., (1994) *Mol. Microbiol.,*

11:375). All are modular proteins of varying degrees of complexity (FIG. 1), but with two features in common: a catalytic doman (CD) and a cellulose-binding domain (CBD) which can function independently (see Millward-Sadler et al., (1994) *Mol. Microbiol.,* 11:375; Gilkes et al., (1988) *J. Biol. Chem.,* 263:10401; Meinke et al., (1991) *J. Bacteriol.,* 173:7126; and Coutinho et al., (1992) *Mol. Microbiol.,* 6:1242). In four of the enzymes, CenB, CenD, CbhA and CbhB, fibronectin type III (Fn3) repeats separate the N-terminal CD from the C-terminal CBD. The CDs of the enzymes come from six of the families of glycoside hydrolases (see Henrissat (1991) *Biochem. J.,* 280:309; and Henrissat et al., (1993) *Biochem. J.,* 293:781); all of the enzymes have an N- or C-terminal CBD from family II or CBDs (see Tomme et al., *Adv. Microb. Physiol.,* in press); CenC has tandem CBDs from family IV at its N-terminus; CenB and XylD each have a second, internal CBD from families III and II, respectively. Cex and XylD are clearly xylanases; however, Cex, but not XylD, has low activity on cellulose. Nonetheless, like several other bacterial xylanases (see Gilbert et al., (1993) *J. Gen. Microbiol.,* 139:187), they have CBDs. Similar systems are produced by related bacteria (see Wilson (1992) *Crit. Rev. Biotechnol.,* 12:45; and Hazlewood et al., (1992) *J. Appl. Bacteriol.,* 72:244). *C. fimi* probably produces other β-1,4-glycanases. The unrelated bacterium, *Clostridium thermocellum,* for example, produces twenty or more β-1,4-glycanases (see Beguin et al., (1992) *FEMS Microbiol. Lett.,* 100:523).

Exemplary of a consensus sequence of a binding domain is the consensus sequence for the cellulose binding domain shown in FIG. 1, which is exemplified by the endoglucanase C N1 binding domain. The probes can be considerably shorter than the entire sequence but should be at least 10, preferably at least 14, nucleotides in length. Longer oligonucleotides are also useful, up to the full length of the gene, preferably no more than 500, more preferably no more than 250, nucleotides in length. RNA or DNA probes can be used. Generally, the binding remains encoded by the nucleotides so identification will show at least about 40% homology (including as appropriate allowances for conservative substitutions, gaps for better alignment and the like) with the binding region and will bind to a soluble B-1,4-glucan with a Ka of $\geq 10^3$ M. Analyses of amino acid sequence comparisons can be performed using programs in PC/Gene (IntelliGenetics, Inc.). PCLUSTAL can be used for multiple sequence alignment and generation of phylogenetic trees.

In use, the probes are typically labeled in a detectable manner, for example, with $^{32}$P, $^3$H, biotin or avidin) and are incubated with single-stranded DNA or RNA from the organism in which a gene is being sought. Hybridization is detected by means of the label after single-stranded and double-stranded (hybridized) DNA (or DNA/RNA) have been separated (typically using nitrocellulose paper). Hybridization techniques suitable for use with oligonucleotides are well known to those skilled in the art. Although probes are normally used with a detectable label that allows easy identification, unlabeled oligonucleotides are also useful, both as precursors of labeled probes and for use in methods that provide for direct detection of double-stranded DNA (or DNA/RNA). Accordingly, the term "oligonucleotide probe" refers to both labeled and unlabeled forms.

In order to isolate the PBP of a polysaccharidase or a polysaccharide binding protein, several genetic approaches can be used. One method uses restriction enzymes to remove a portion of the gene and then to fuse the remaining gene-vector fragment in frame to obtain a mutated gene that encodes a truncated protein. Another method involves the use of exonucleases such as Bal31 to systematically delete nucleotides either externally from the 5' and the 3' ends of the DNA or internally from a restricted gap within the gene. These gene deletion methods result in a mutated gene encoding a shortened protein molecule which can then be evaluated for substrate or polysaccharide binding ability. Appropriate substrates for evaluating and binding activity include those listed in Table 2, above.

Once a nucleotide sequence encoding the polysaccharide binding region has been identified, either as cDNA or chromosomal DNA, it can then be manipulated in a variety of ways to prepare a composition where the expression product has a structure represented by formula (1) above. The nucleotide sequence may be fused to a DNA sequence encoding a polypeptide of interest. It is highly desirable that the three-dimensional structure of the component polypeptides be retained. Depending upon the source of the fragments and the length of the desired polypeptide, the restriction can be designed into the synthetic genes used to construct chimeric polypeptides. If possible, the restriction site(s) leaves the amino acid sequence of the polypeptide unaltered. However, in some case incorporation of a new restriction site(s) may yield an altered amino acid sequence without changing the activity of the protein.

During construction of the expression cassette, various fragments of the DNA usually are cloned in an appropriate cloning vector, which allows for amplification of the DNA, modification of the DNA or manipulation by joining or removing of sequences, linkers, or the like. Normally, the vectors are capable of replication in at least a relatively high copy number in bacteria. A number of vectors are readily available for cloning in gram-negative bacteria, especially *E. coli,* including such vectors as pBR322, pTZ, pUC and the like. The cloning vectors are characterized by having an efficient replication system functional in the host bacterium.

The cloning vector has at least one unique restriction site, usually a plurality of unique restriction sites, and may also include multiple restriction sites. In addition, the cloning vector will have one or more markers which provide for selection of transformants. The markers will normally provide resistance to cytotoxic agents such as antibiotics, heavy metals, toxins or the like, complementation of auxotrophic host, or immunity to a phage. By appropriate restriction of the vector and the cassette, and, as appropriate, modification of the ends, by chewing back or filling in overhangs, to provide for blunt ends, by addition of linkers, by tailing, complementary ends can be provided for ligation and joining of the vector to the expression cassette or component thereof.

After each manipulation of the DNA in the development of the cassette, the plasmid is cloned and isolated and, as required, the particular cassette component analyzed as to its sequence to insure that the proper sequence has been obtained. Depending upon the nature of the manipulation, the desired sequence can be excised from the plasmid and introduced into a different vector or the plasmid may be restricted and the expression cassette component manipulated, as appropriate.

In some instances, a shuttle vector is employed where the vector is capable of replication in different hosts requiring different replication systems. This may or may not require additional markers which are functional in the two hosts Where such markers are required, these can be included in the vector, where the plasmid containing the cassette, two replication systems and the marker(s) may be transferred from one host to another, as required. For selection, any useful marker may be used. Desirably, resistance to neomycin or tetracycline are of interest. However, although a marker for selection is highly desirable for convenience, other procedures for screening transformed cells are known to those skilled in the art, for example, transformed cells can be screened by the specific products they make; synthesis of the desired product may be determined by immunological or enzymatic methods.

The DNA encoding the fusion protein can then be manipulated in a variety of ways to provide for expression. Illustrative transcriptional regulatory regions or promoters include, for bacteria, the lac promoter, lambda left and right promoters, trp and lac promoters, Tac promoter, and the like. The transcriptional regulatory region may additionally include regulatory sequences which allow the time of expression of the fused gene to be modulated, for example, the presence or absence of nutrients or expression products in the growth medium, temperature, etc. For example, expression of the fused gene can be regulated by temperature using a regulatory sequence comprising the bacteriophage lambda PL promoter, the bacteriophage lambda OL operator and a temperature sensitive repressor. Regulation of the promoter is achieved through interaction between the repressor and the operator. A preferred promoter is the strong glucose-repression insensitive Tac promoter. Examples of high level expression vectors are described in Graham et al., (1995) Gene 158:51–54.

The expression cassette can be included within a replication system for episomal maintenance in an appropriate cellular host or can be provided without a replication system, where it can become integrated into the host genome. The DNA can be introduced into the host in accordance with known techniques, such as transformation, using calcium phosphate-precipitated DNA, transfection by contacting the cells with a virus, microinjection of the DNA into cells or the like.

Once the fusion protein DNA has been introduced into the appropriate host, the host can be grown to express the fusion protein. Microbial hosts can be employed which can include, for example, bacteria such as *E. coli*, and eukaryotes such as Saccharomces, particularly *S. cerevisiae*, Streptomyces, *Bacillus Pichia pastoris*, or mammalian cells such as BHK and CHO. The recombinant products can be glycosylated or non-glycosylated, having the wild-type or other glycosylation. The amount of glycosylation depends in part upon the sequence of the particular peptide, as well as the organism in which it is produced. Thus, expression of the product in *E. coli* cells results in an unglycosylated product, and expression of the product in insect cells generally results in less glycosylation than expression of the product in mammalian cells. Expression in yeast can result in hyperglycosylation.

For isolation of the fusion protein, where the product is retained in the host cell, the cells are harvested, lysed and the product separated, isolated and/or purified using the phase separation system. In some instances, it can be desirable to provide for a signal sequence (secretory leader) upstream from and in reading frame with the structural gene, which provides for secretion of the fusion protein. Illustrative secretory leaders include the secretory leaders of penicillinase, immunoglobulins, T-cell receptors, outer membrane proteins, and the like. By fusion in proper reading frame the fusion protein can be secreted into the medium. However, in bacterial expression systems such as *E. coli*, a significant fraction leaks into the extracellular media (Ong et al., *Biotech. Bioeng.* (1993) 42:401). Where the product is secreted, the nutrient medium can be collected and the product isolated using the phase separation system. To produce an active protein it can be necessary to allow the protein to refold.

The phase separation systems is combined with the biological fluid, fermentation broth, cell lysate or other source of the biological compound to be purified and phase separation induced. To separate and/or purify a component of an aqueous mixture, following partitioning of the composition comprising the PBP into the oligosaccharide phase, the phases are separated and the composition comprising the PBP dissociated from the polymer phase in any of a variety of ways. These include contacting the separated oligosaccharide phase with a different phase-inducing polymer or salt which extracts the composition comprising the PBP; changing the chemical and/or physical condition, e.g., by adding a dissociating agent to the separated oligosaccharide phase, such as an acid or a base, urea, ethanol, DMSO, and the like, or where the binding reaction was identified as endothermic or exothermic, altering the temperature a sufficient amount so that the binding affinity is decreased; and having the compound of interest from the PDP-oligosaccharide polymer.

Where cleavage is used, the protein of interest or chemical moiety can be cleaved readily from the polysaccharide binding region by the use of a protease specific for a sequence present between the polysaccharide binding region and the protein of interest or the chemical moiety leaving the PBP bound to the oligosaccharide polymer. Preferably, the protease is provided in a form which will facilitate its removal following cleavage of the polypeptide of interest from the PBP. As an example, the cleavage protease can be prepared as a cleavage enzyme complex, wherein the protease is bound to a second polysaccharide binding moiety having a substrate specificity different from that of the first polysaccharide binding moiety bound to the polypeptide of interest and/or having different binding characteristics (Assouline et al. (1993) *Protein Engineering* 6:787–792; Assouline et al. Thus, cleavage of the binding domain from the recombinant protein of interest can be done in solution and the cleavage enzyme complex then removed by binding to a polysaccharide substrate to which the first polysaccharide binding moiety does not bind. Alternatively, the cleavage enzyme complex can be immobilized on a polysaccharide matrix to which the first polysaccharide binding moiety does not bind. (See Assouline et al (1993) supra; Assouline et al (___₁₃) supra) The recombinant protein of interest or chemical moiety is released from the oligosaccharide polymer free of contaminating PBPs which remain bound to the polymer. Alternatively, a non-specific protease can be used to completely degrade the PBP portion of the PBP complex, thus releasing it from the oligosaccharide polymer, for example, by treatment by protease K at a concentration of about 50 $\mu$g/ml for about 20 minutes at about 37° C. Dir et al. (1991) *Bio/Technology*, 9:1096–1099.

In some instances the fusion protein itself may be of interest and therefore it is the fusion protein that is removed from the oligosaccharide polymer, rather than separating the components of the fusion protein. To debind the fusion protein from the oligosaccharide polymer, a low ionic strength buffer or water is required or a buffer of alkaline pH or a chaotropic salt. The temperature for desorption is not critical and generally in the range of 10° C.–40° C., although ambient temperatures are generally preferred, i.e., about 20° C. The fusion protein bound is washed repeatedly in water or diluted by a continuous stream of water. Generally, a pH 9.5 carbonate buffer or 6 M guanidine HCl can be used for this desorption step. Dilute sodium hydroxide (about 0.1 M) may be the preferred treatment in some cases. The nature of the PBP can be modified to alter its adherence properties so that it can be, or, if desired, cannot be, desorbed by water. Application of the desorption medium to the matrix causes release of the fusion protein from the oligosaccharide polymer. For isolation of the PBP-conjugate following release from the substrate, various techniques may be used. For example, the polysaccharide surface can be washed free of the PBP-conjugate with the desorption solution as described above. The PBP-conjugate can be separated from the desorption solution, for example, by changing its ionic strength of pH and readsorbing the PBP-conjugate on an ion exchange medium or on a second polysaccharide matrix.

The affinity phase separation system has many uses. These include concentrating a component in a mixture, purifying a component in a mixture, where the purifying can be two-fold, generally greater than twenty-fold, and can include up to purification of 80 to 90%. The fold purification can be measured relative to removal of contaminants, increase in specific activity, and the like. For some applications, the method also can be used for cell separation and/or enrichment in a particular cell type. For example, a population of stem cells can be enriched by contacting the cells with the PBP alone which binds to carbohydrate residues on the surface of the cells, or with PBP to which a first member of a specific binding pair is fused, for example a receptor ligand, for example, a peptide hormone or other hormone where the second member of the specific binding pair, i.e., the receptor, is present on the cell surface. Other ligands which can be used include antibodies, such as anti-CD34 and cytokines, such as IL-2. Following affinity-phase partitioning, the cells can be released from the separated oligosaccharide polymer phase, for example, using trypsin. The shear forces in the affinity-phase partitioning system are significantly less than in other cell-separation methods resulting in less damage to the separated cells.

Other uses of the technology include extractive bioconversion, i.e., methods for partitioning reaction products, particularly in enzymatic processes where the product is a feedback inhibitor of the enzymatic reaction. In such a system, the enzyme is bound to a PBP so that the enzyme retains enzymatic activity. The substrate for the enzyme is one which either naturally partitions into the oligosaccharide polymer phase or which is bound to a PBP, and the product is one which does not remain in the oligosaccharide polymer phase, but rather partitions into the second component, such as when the product is more hydrophobic than the substrate. The second component of the system is then removed and the product recovered. Examples of enzymatic reactions which can be used with the extractive bioconversion system include transglycosylation, for example, for preparation of β-1,4-linked oligosaccharide sweeteners; mixed transesterification, for example for conversion of low value fatty acids to high value fatty acids and glycerol production; and for peptide synthesis. The subject compositions which retain the PBP, can be used as a means of immobilizing the compound of interest on a polysaccharide support, since the PBP adsorption to its substrate is strong and specific.

The immobilized systems find use, for example, in preparing solid state reagents for diagnostic assays, the reagents including enzymes, antibody fragments, peptide hormones, etc.; drug binding to decrease clearance rate where the cellulose can be either soluble, for example, carboxymethyl cellulose or a solid support such as microcrystalline cellulose (Avicel) where the drug is a polypeptide such as interleukin 2; drug delivery, for example, bound to carboxymethyl cellulose and can be used in conjunction with binding of an adjuvant to the same cellulose support, for example, for enhancement of immunospecificity of the drug to be delivered; dye binding, for example, coupling of paints or dyes to polysaccharide, for example, cellulosic surfaces; printing on, for example, paper and cloth (cotton); and to provide hydrolysis or synergy, for example, targeting of enzymes such as ligninase for treatment of wood chips, targeting of porphyrins, for example, for bleaching of wood pulp; agricultural uses such as binding of insecticides to plant surfaces, for example, Bt toxin or other antimicrobials; for nitrogen fixation, for example, for binding of organisms to root surfaces; sustained fertilizer release; and sustained release of fungicides. They can also be used under conditions of high salt such as in a marine environment for anti-fouling of surfaces exposed to sea water where transfer to fresh water removes the fusion protein.

Examples of biologicals which can be purified in this way include interleukin 2, Factor X, ligninase, and TPA, or any other polypeptide or protein which can be fussed to a PBP. Other examples include culture broth (from prokaryotic or eukaryotic cell or tissue cultures), biological fluids, tissue extracts, extracts from cell lysalts, including bacterial, fungal, plant, animal, fish, and fowl, particularly purified protein, and the like. Generally, the mixture is clarified prior to application to the affinity partitioning system to remove cellular debris.

The following examples are offered by way of illustration and not by way of limitation.

EXAMPLES

Abbreviations pNPC=p-nitrophenyl-β-D-cellobioside;

HPA=hide powder axure;

gCenA and gCex=the glycosylated forms of CenA and Cex from *C. fimi*;

ngCenA and ngCex=the non-glycosylated forms of CenA and Cex from recombinant *E. coli*;

RPC=reverse-phase chromatography;

SDS-PAGE=sodium dodecyl sulfate-polyacrylamide gel electrophoresis;

α-Pro/Thr=rabbit antiserum directed against synthetic Cex Pro/Thr box;

PMSF=phenyl-methylsulfonyl fluoride.

Biological Culture Deposits

The following deposits have been made with the American Type Culture Collection (ATCC), 12301 Park Lawn Drive, Rockville, Md. 20852. A derivative of the cloned gene CenA on plasmid pcEC-2 in *Eschenchia coli* C600 was deposited on Apr. 23, 1986 and given ATCC Accession No. 67101. A derivative of the cloned gene Cex on plasmid pEC-1 was deposited on May 27, 1986 and given ATCC Accession No. 67120. *E. coli* JM83, pUC12-1.1 lcex was deposited on Apr. 23, 1986 and given ATCC Accession No. 67102. The full nucleotide sequences of pTugA (Accession Number L24193) pTugAS (Accession Number L24367), *C. fimi* CenA (Accession Number M15823), and *C. fimi* CenC (Accession Number X57858) have been deposited with GenBank.

Materials

Klucel or HPC is supplied by Aqualon. HPC is derived from a cellulose molecules and is also known as cellulose 2-hydroxypropyl ether.

Natrosol or HEC is supplied by Aqualon. HEC is a modified cellulose polymer containing hydroxyethyl side chains and is also known as cellulose 2-hydroxyethyl ether. HEC is a white, non-ionic powder. HEC is also marketed under the following tradenames: Alcoramnosan/Liporamnosan (Vevy);Tylose H Series (Hoechst Celanese/Colorants & Surf.)

Bermocoll E or EHEC is supplied by Berol Nobel AB. EHEC is an ethylene glycol ether of ethyl cellulose. EHEC is also marketed by Aqualon under the tradename Aqualon EHEC.

Hydroxypropylmethyl Cellulose (HPMC) is supplied by Sigma. HPMC is a propylene glycol ether of methyl cellulose and also known as methylhydroxypropyl cellulose. HPMC is also marketed under the following tradenames: Benecel/Culminal HPMC (Aqualon); Viscontran MHPC (Henkel)

Dextran is supplied by Pharmacia Biotech.

Pluronics are supplied by BASF. Pluronic is a block copolymer of ethylene oxide and propylene oxide. Both solid forms (F-series) and paste forms (P-series) of the Pluronics can be used.

Example 1

Isolation of $CBD_{N1}$

*Escherichia coli* JM101 (SupE, thi-1, $_\Delta$(tac-proAB), [F'traD36, proAB, tacIqZd$_\Delta$M15] (Yanish-Perron et al. *Gene* (1985) 33:103–119) was used as the host strain for maintenance of the plasmids and for production of recombinant protein. Cultures were grown at 30° C. in liquid tryptone-yeast extract-phosphate medium (TYP) or on Luria broth (LB agar, supplemented with kanamycin (100 µg/ml).

Figure 5:
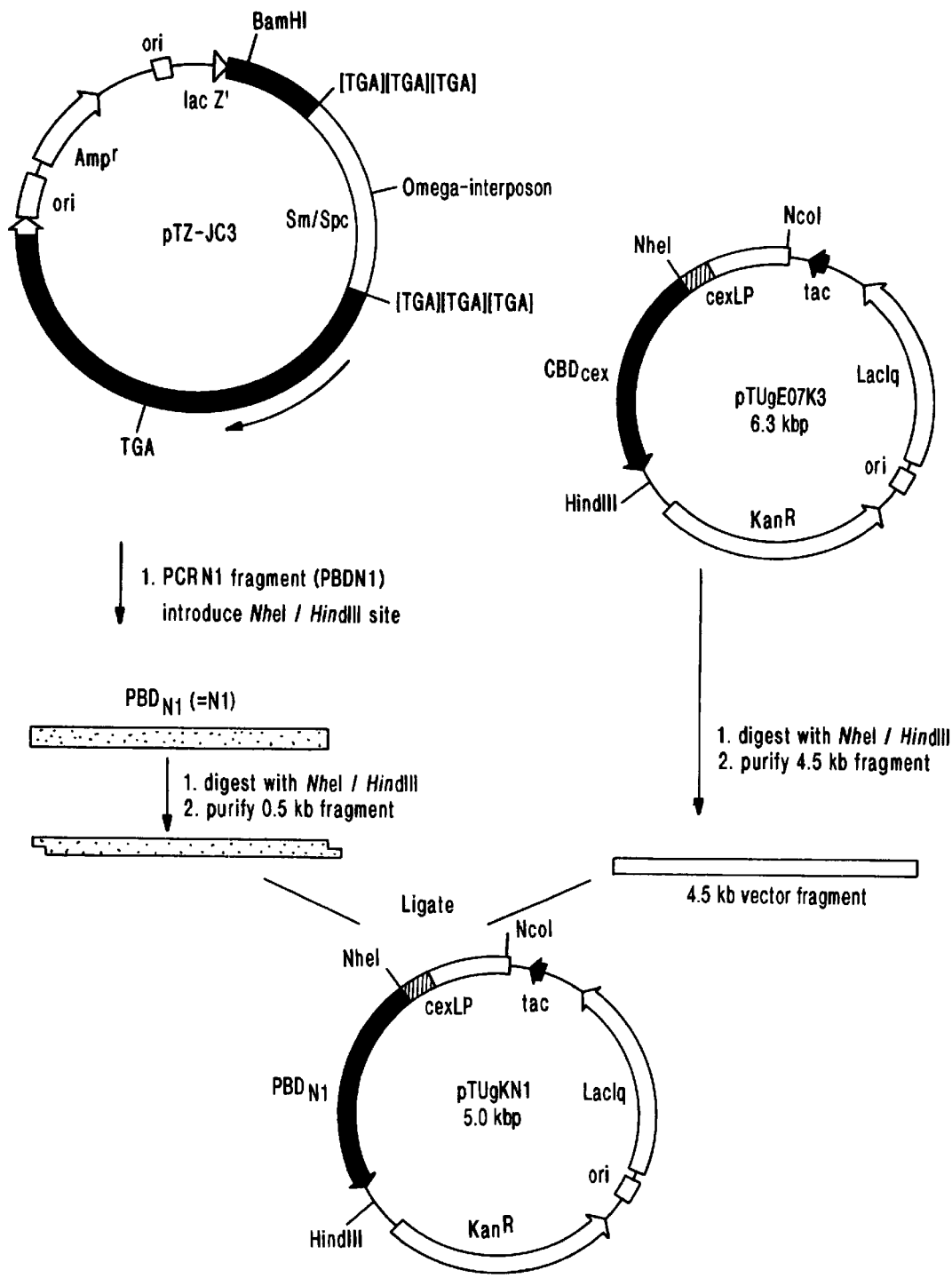
FIG. 5 shows the construction of pTugKN1. pTugE07K3 was digested completely with NheI and HindIII to remove the 1.8 kbp fragment containing the $CBD_{Cex}$ and the 4.5 kbp fragment was isolated. PCR was used to introduce appropriate restriction sites at the 5' and 3' ends of the gene fragment encoding $CBD_{N1}$. A NheI site (underlined), coinciding with the N-terminal end (ala-ser) of mature $CBD_{N1}$, as introduced as a silent mutation at the 5' and of cbdN1 using the oligonucleotide 5'-TTACCTCATATGGCTAGC-CGATCGGGGAGGGAACG-3'. (SEQ ID NO:12) A HindIII site was introduced at the 3' end of cbdN1 using the oligonucleotide 5'-AGAATGAATTCAAGCTTAGAGCT-CGACCTCGGAGTC-3'(SEQ ID NO:13). A translational stop codon was also included in this primer. The polymerase reaction (PCR) mixture (50 µl total volume) contained 10–100 ng template DNA(pTZ-JC3) (Coutinho et al. *Mol. Microbiol.* (1992) 6:1243–1252), 25–50 pmole (300 ng) primers, 2 mM $MgCl_2$, 6% dimethyl sulfoxide, 0.2 mM 2'-deoxynucleotide 5'-triphosphates and 1 unit Taq DNA polymerase in 50 mM Tris. HCl buffer, pH 8.3. Twenty-eight successive cycles were performed as follows: denaturation at 94° C. for 15 sec, annealing at 57° C. for 1.4 min and primer extension at 72° C. for 1.5 min. The resulting $CBD_{N1}$ PCR fragment was digested completely with NheI and HindIII and the 0.5 kbp fragment was purified by precipitation. The 4.5 kbp and 0.5 kbp fragments were ligated to give pTugKN1.
Figure 7:
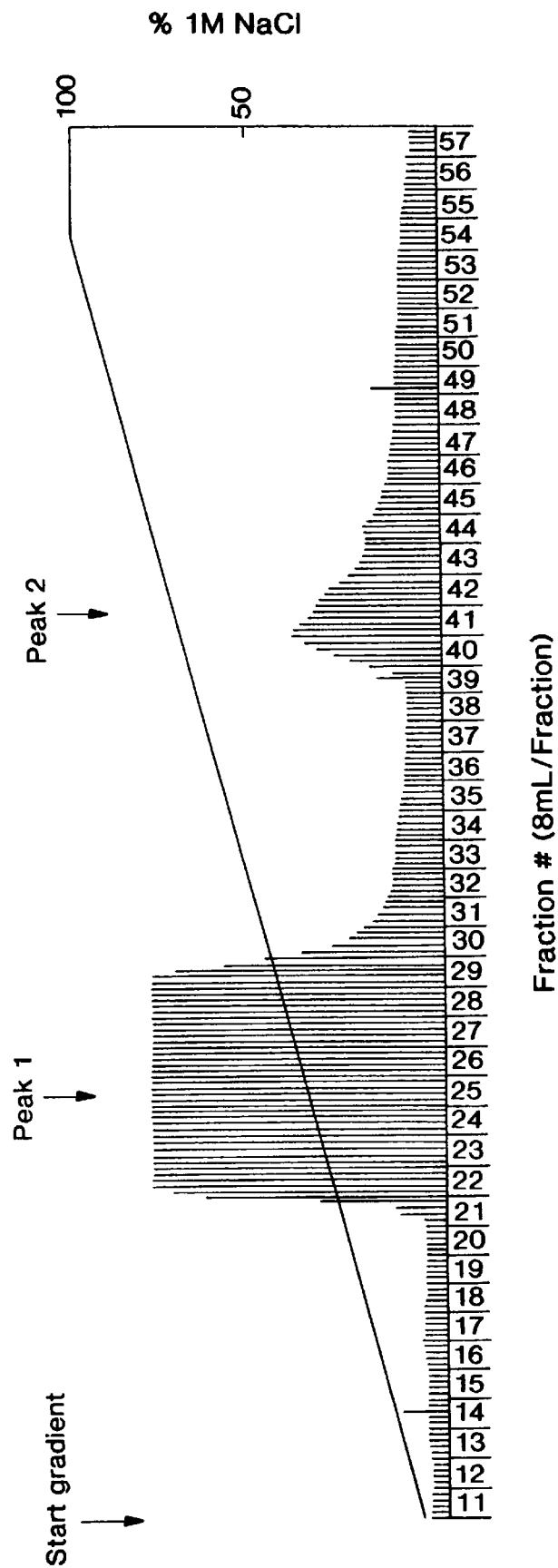
FIG. 7 shows the results of anion exchange chromatography of $PBD_{N1}$. Partially purified $PBD_{N1}$ (150 mg in 200 ml) was loaded (1 ml/min) onto an anion exchange column (MonoQ) equilibrated in 20 mM potassium phosphate buffer, pH 6.0. After washing the column with 200 ml buffer, pH 6.0 bound protein was recovered (8 ml fractions) using a salt gradient (600 ml, 0–1 M NaCl in 20 mM potassium phosphate buffer, pH 6.0). $PBD_{N1}$ was recovered from the column in 300 mM salt (peak 1). Contaminating proteins bound more tightly and were removed in higher salt (peak 2).
Figure 8:
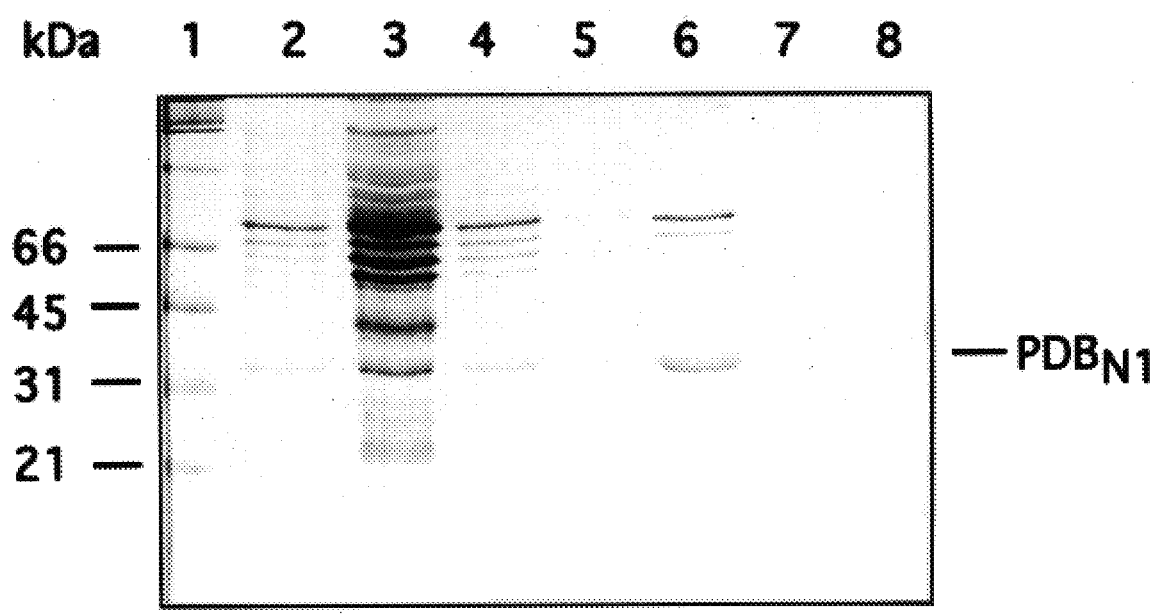
FIG. 8 shows SDS-PAGE analysis of $PBD_{N1}$ during purification from culture supernatants. Culture supernatants from JM101 harboring pTugKN1 (induced) (lane 2), whole culture suspension (cells and broth) (lane 3), Avicel fraction after binding of proteins in culture supernatants (lane 4), flow through fraction after binding supernatants to Avicel (lane 5), fraction eluted with $H_2O$ from Avicel (lane 6) and $PBD_{N1}$ after MonoQ purification (lanes 7 and 8) were analysed on a gel containing 12.5% acrylamide. Molecular mass standards (lane 1) are as indicated.

Overnight cultures of *E. coli* strain JM11, harboring pTugKN1 (see FIG. 5), were diluted 500-fold in TYP supplemented with 100 µg kanamycin/ml, and grown at 30° C. to an optical density of 2.0–3.0. $PBD_{N1}$ production was induced by the addition of isopropyl-1-thio-β-D-galactopyranoside (IPTG) to a final concentration of 0.1 M and the bacteria were incubated for a further 18 h at 30° C. Culture supernatants was clarified by centrifugation (4° C.) for 10 min at 13000× g and cells were disgarded. Affinity chromatography on cellulose was used to purify $PBD_{N1}$, as follows. The clarified culture supernatant was incubated (4° C.) with microcrystalline cellulose (Avicel) (50 mg. L$^{-1}$) with occasional stirring to allow $PBD_{N1}$ to bind. The cellulose suspension was filtered on a Buichner funnel through a glass filter (Whatman GF/A) and briefly washed with 1 M NaCl in 50 mM potassium phosphate, pH 7.0. Bound $PBD_{N1}$ was desorbed with water and concentrated by ultra filtration. Partially purified $PBD_{N1}$ was then loaded onto an anion-exchange color (MonoQ) equilibrated in 20 mM potassium phosphate-buffer, pH 6.0, operated at a flow rate of 1 ml./min. Proteins bound tightly to the column and were removed with a salt gradient (0-IN NaCl, pH 6.0) (see FIG. 7). $PBD_{N1}$ was recovered in 300 mM salt (peak 1, FIG. 7). Contaminating proteins bound more tightly and were removed in higher salt (peak 2, FIG. 7).

Example 2

Figure 9A:
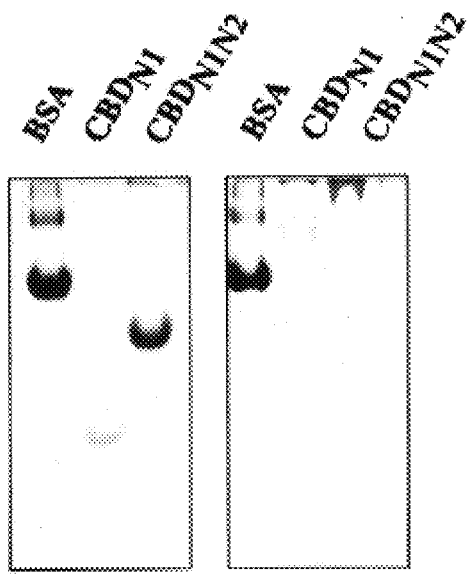
FIGS. 9A through 9C show affinity electrophoresis gels for analysis of PBPs ($PBD_{N1}$ and $PBD_{N1N2}$). Binding of purified Bovine Serum Albumin (BSA) (lane 1), $PBD_{N1}$ (lane 2) and $PBD_{N1N2}$ (lane 3) to soluble oligosaccharides was analysed in native gels containing 13% acrylamide. Retardation in the gels in the presence (+) of polysaccharide ((0.1% w/v) hydroxyethyl cellulose (HEC) or barley glucan) relative to their migration in gels in the absence (−) of the oligosaccharides is indicative of binding. Xylan is used as an non-binding polysaccharide. 5 µg of each protein were loaded on each gel.
Figure 9B:
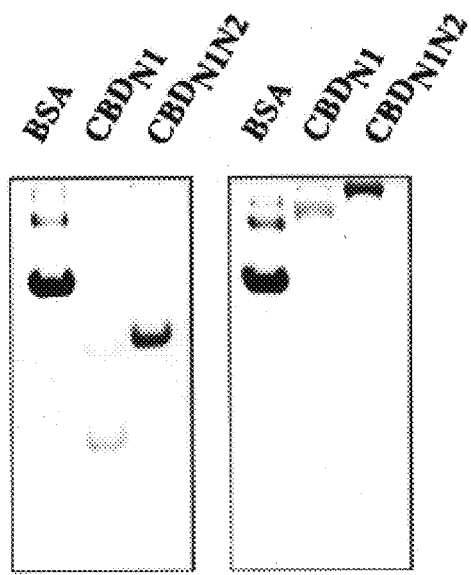
Figure 9C:
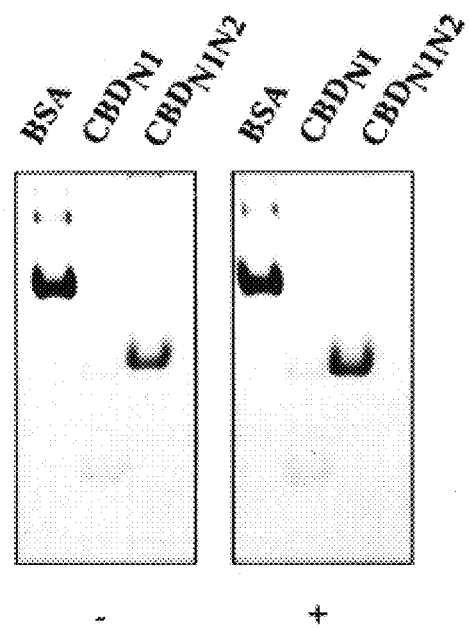

Analysis of HEC, Barley β-glucan and Xylan Binding to $CBD_{N1}$ and $CBD_{N1N2}$ by Affinity Electrophoresis Affinity electrophoresis (Mimura et al. (1992) *J. Chromatography* 597:345–350) was used to identify and evaluate the binding of $CBD_{N1}$ and $CBD_{N1N2}$ to soluble polysaccharides with a DP≧15 such as HEC and barley β-glucan. The original continuous disc electrophoresis method was replaced with a discontinuous method. Two native gels, one containing the polysaccharide (0.1% w/v) and one without the ligand, were prepared next to one another in the same plate of a BioRad electrophoresis system. This guaranties that analysis in the presence or absence of soluble polysaccharide is conducted essentially under the same conditions and that the observed effects (retardation in the presence of binding glucan) are not the result of an anomalous electrophoretic migration. BSA was used as a negative control in each gel. Proteins (5 mg each) were loaded onto the gels. Electrophoresis was conducted at 4° C. under native conditions at pH 8.2–8.8 for 2 to 3 h. $CBD_{N1}$ and $CBD_{N1N2}$ interact strongly with HEC and barley β-glucan and as a result, their migration in the gels containing these oligosaccharides (+) is severely retared as compared to the migration in gels in absence (−) of a β-glucan (see FIGS. 9A and 9B). $CBD_{N1}$ and $CBD_{N1N2}$ do not exhibit any affinity for xylan and no retardation of migration in the gels is observed in the presence of this glycan as compared to migration in its absence (see FIG. 9C). $N_1$ and N1N2 refers to $CBD_{N1}$ and $CBD_{N1N2}$, respectively.

Example 3

Figure 15:
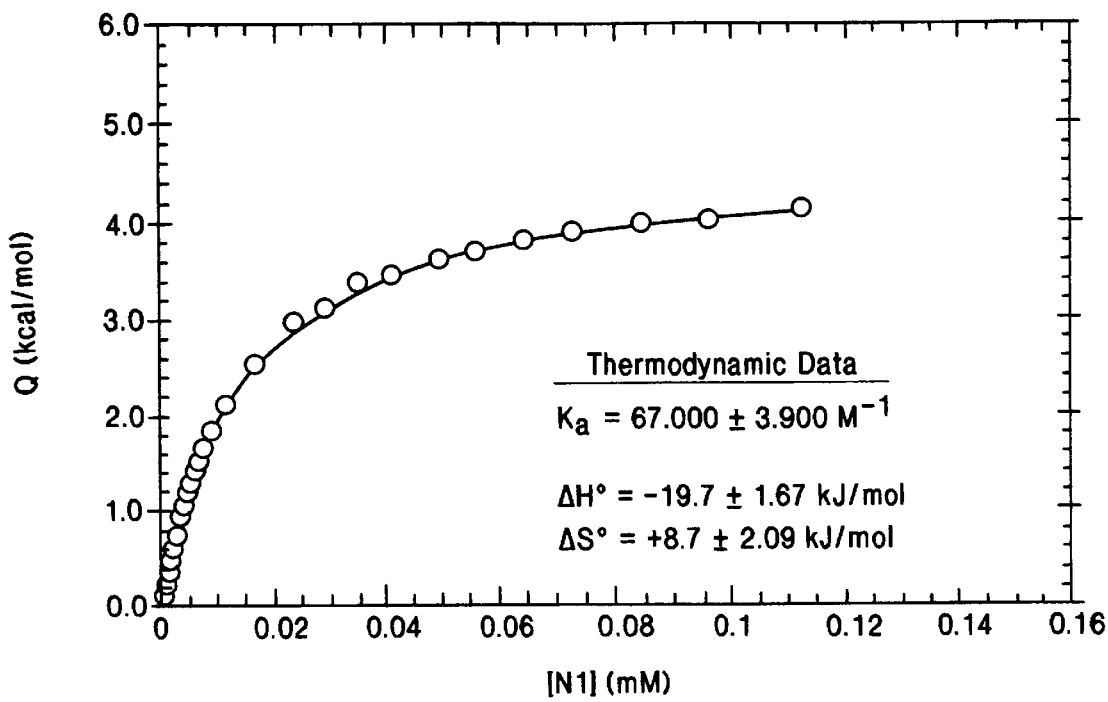
FIG. 15 shows isothermal titration microcalorimtery data for binding of hydroxyethyl cellulose to $CBD_{N1}$ in 50 mM phosphate buffer solution at pH7 and 35° C.

Isothermal Titration Microcalorimetry Determination of Oligosaccharide Binding Constants for $CRD_{N1}$ and $CBD_{N1}$-Fusion Proteins Microcalorimetry was used to measure binding thermodynamics for $CBD_{N1}$ to a wide range of water-soluble oligosaccharides with the aim of identifying a set of suitable ligands for the affinity partition system. These data are shown in Table 7 below. FIG. 15 shows reversible binding-isotherm data measured with a Calorimetry Sciences Corp. model 4200 ITC for $CPD_{N1}$ binding to hydroxyethyl cellulose (HEC) in 50-mM PBS at 35° C. and pH 7. $CPD_{N1}$ strongly binds HEC with an equilibrium binding constant in the range of weak antibody-antigen interactions. Barley β-glucan binding to $CPD_{N1}$ is even stronger at these conditions ($K_a$=85,500 M$^{-1}$). For both oligosaccharides, $CPD_{N1}$ binding is as tight or even tighter than nearly all PEG-based affinity ligands (e.g., Cibacron blue-PEG, Procion red-PEG, dinitrophenyl-PEG, diacetic acid-PEG) currently in use in affinity partition systems. This relatively high binding affinity, combined with the potential for a single oligosaccharide chain to bind multiple $CPD_{N1}$-fusion proteins, suggests that both capacity and selectivity will be high in this affinity partition system. A summary of N1 binding thermodynamics is provided in Table 8 below. Binding of $CPD_{N1}$ to both HEC and barley β-glucan is strongly exothermic, indicating that binding will increase at lower temperatures and that temperature decrease can be used in the partition step and temperature elevation in elution steps.

Example 4

Phase-Equilibrium Analysis of Mixtures of HEC and Pluronic P105

Figure 16:
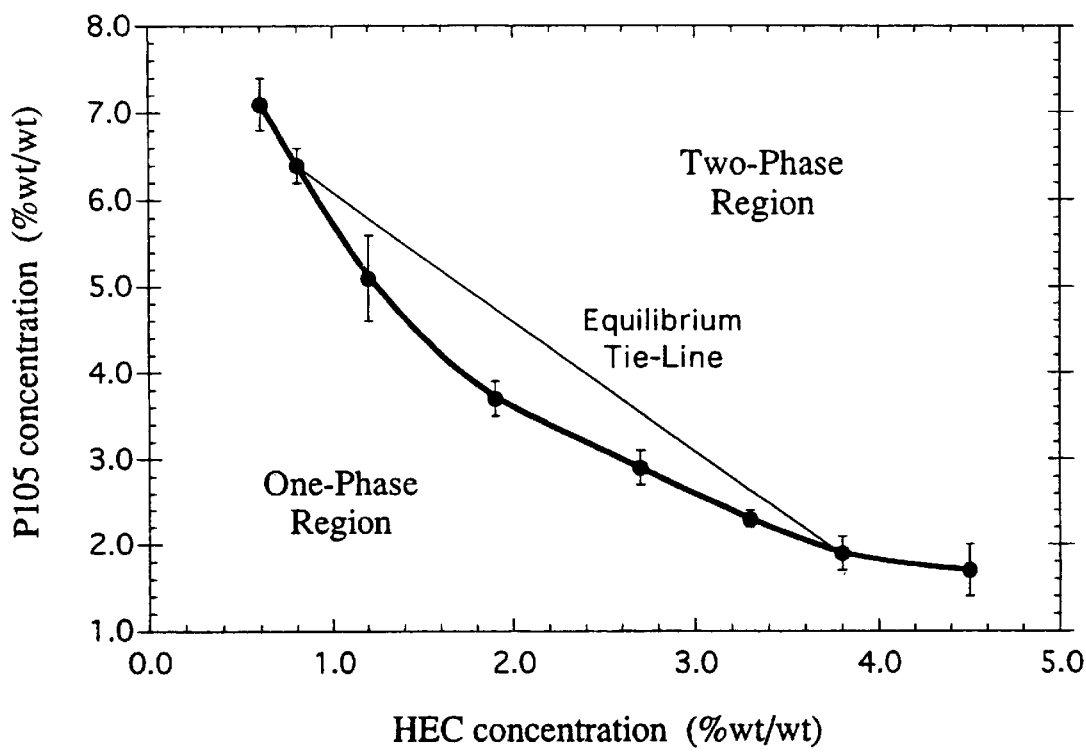
FIG. 16 shows preliminary phase-equilibria data for mixtures of hyroxyethyl cellulose and Pluronic P105 in 50 mM PBS at 35° C. and pH7.

Phase-equilibria data were obtained using the procedure of Haynes et al. (*Fluid Phase Equilibria*, (1989) 53:463) for mixtures of HEC and Pluronic P105 (a poly(ethylene glycol)-poly(propylene glycol) copolymer) in 50-mM PBS at 35° C. and pH 7. As shown in FIG. 16, a stable two-phase partition system is formed at any total polymer concentrations above ca. 3% (wt/wt) Pluronic P105 and 2% HEC, giving a fairly large range of two-phase compositions and equilibrium tie-line lengths useful for affinity partitioning.

TABLE 7

Binding Specificity of $CBD_{N1}$ from Endoglucanase C of *Cellulomonas fimi*

| Ligand | Binding to $CBD_{N1}{}^a$ | Detection method |
|---|---|---|
| Soluble ligands | | |
| Glucose | − | NMR |
| Cellobiose | − | NMR |
| Cellotriose | +/− | NMR/calorimetry |
| Cellotetraose | ++ | NMR/calorimetry |
| Cellopentaose | +++ | NMR/calorimetry |
| Cellohexaose | +++ | NMR/calorimetry |
| Methylcellulose (MC) | ++ | affinity electrophoresis |
| Carboxymethylcellulose (CMC) | + | affinity electrophoresis/competition assay |
| Ethylhydroxyethylcellulose (EHEC) | ++ | affinity electrophoresis |
| Hydroxyethylcellulose (HEC) | +++ | affinity electrophoresis/competition assay |
| Hydroxypropylmethylcellulose (HPMC) | +++ | affinity electrophoresis |
| Barley β-glucan | +++ | calorimetry/affinity electrophoresis/competition assay |
| Oat β-glucan | +++ | calorimetry/affinity electrophoresis |
| Chitosan | +/− | affinity electrophoresis |
| Glucomannan | + | affinity electrophoresis |
| Mannan | − | affinity electrophoresis |
| Xylan | − | affinity electrophoresis/competition assay |
| Arabinogalactan | − | affinity electrophoresis |
| Starch (amylopectin) | − | affinity electrophoresis |
| Dextran T70 | − | affinity electrophoresis |
| Laminarin | − | affinity electrophoresis |
| Insoluble ligands | | |
| Phosphoric acid swollen cellulose (PASC) | +++ | binding isotherms |
| Avicel | + | binding isotherms |
| Bacterial microcrystalline cellulose (BMCC) | − | binding isotherms |
| Tunicin cellulose | − | binding isotherms |
| Chitin | +/− | binding isotherms |
| Amylose | − | binding isotherms |
| Sephadex | +/− | binding isotherms |
| Pachyman | − | binding isotherms |

TABLE 8

Summary of N1 Binding Thermodynamics at 35° C.

| | NMR | Isothermal Titration Microcalorimetry | | |
|---|---|---|---|---|
| Ligand | $K_a$ $(M^{-1})$ | $K_a$ $(M^{-1})$ | $\Delta H°$ (Kcal/mol) | $-T\Delta S°$ (kcal/mol) |
| Cellotriose | 180 ± 50 | n.m. | — | — |
| Cellotetrose | 4200 ± 700 | 4100 ± 500 | −6.4 ± 0.2 | 1.4 ± 0.1 |
| Cellopentose | 34000 ± 7500 | 17900 ± 3100 | −6.8 ± 0.2 | 0.86 ± 0.1 |
| Cellohexose | 51000 ± 18000 | 25200 ± 3900 | −6.9 ± 0.2 | 0.79 ± 0.1 |
| Barley β-Glucan | n.m. | 85500 ± 4400 | −7.3 ± 0.1 | 0.48 ± 0.1 |
| HEC | n.m. | 67000 ± 3900 | −7.2 ± 0.1 | 0.50 ± 0.1 |

Example 5

Isothermal Titration Microcalorimetry Determination of Suitable Elution Conditions for $CBD_{N1}$ from an Oligosaccharide Polymer ITC is also used to determine suitable elution conditions by measuring equilibrium dissociation constants as a function of temperature, salt concentration and type, and concentration of cosolvents, such as ethylene glycol or urea, designed to disrupt the favorable hydrogen-bond structure of the $PBP_{N1}$-carbohydrate complex.

Example 6

Figure 10A:
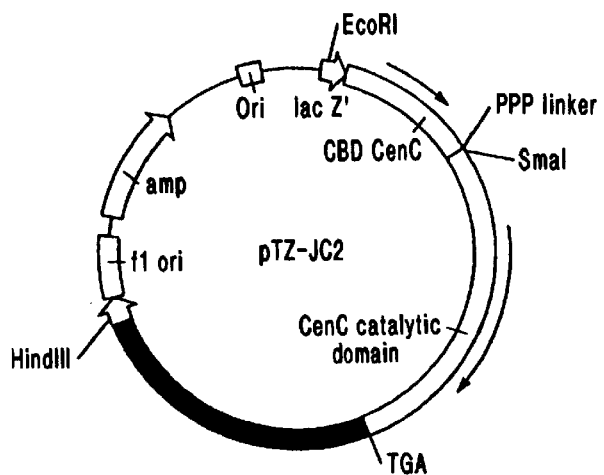
FIGS. 10A through 10C show the vectors used in the construction of pTZ-JC13 (FIG. 10C).
Figure 10B:
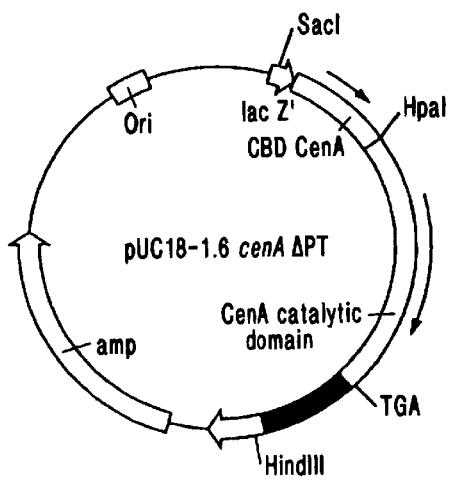
Figure 10C:
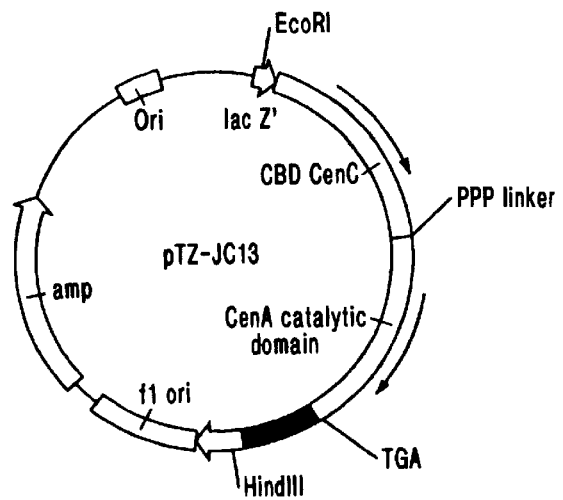
Figure 11:
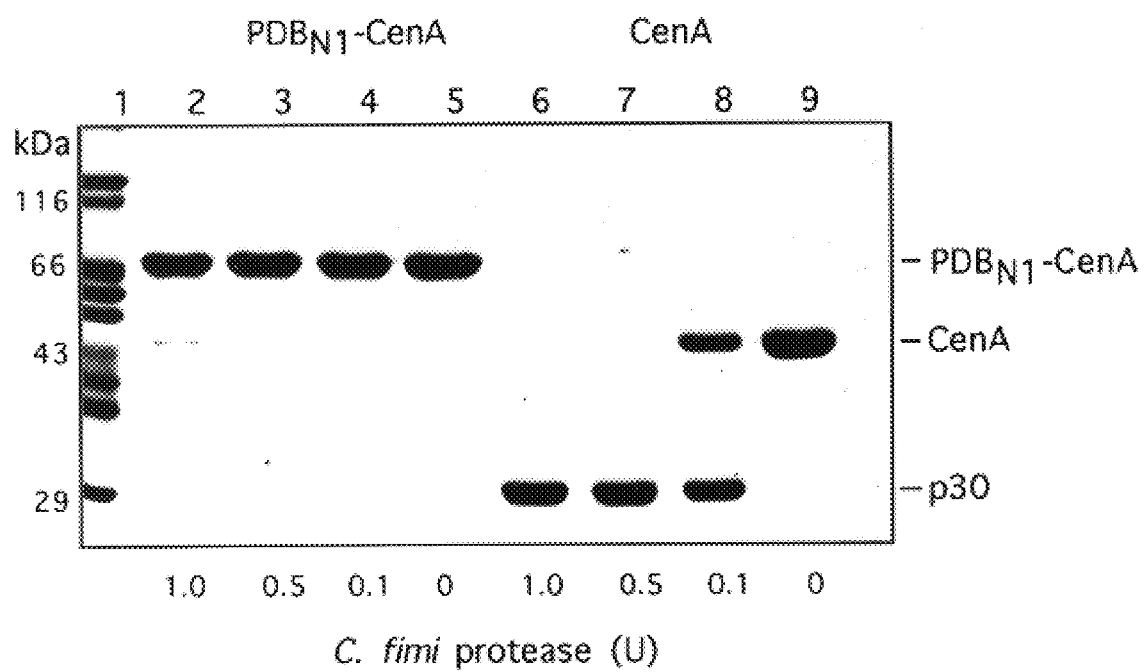
FIG. 11 shows the results of analysis of proteolysis products from CenA and the $PBD_{N1}$-CenA fusion protein using SDS-PAGE analysis. Eight µg of each polypeptide was incubated in 50 pl phosphate-buffer, pH 7.0 (50 mM) with 0 (lanes 5 and 9), 0.1 (lanes 4 and 8), 0.5 (lanes 3 and 7) or 1.0 units (lanes 2 and 6) of *C. fimi* protease for 3 h at 30° C. Reaction products were analysed on gels containing 12.5 % acrylamide. Molecular mass markers (lane 1) are as indicated. P30 corresponds to the catalytic domain of CenA after proteolytic removal of the cellulose-binding domain (Gilkes et al. *J. Biol. Chem* (1988) 263:10401–10407).

Construction of Expression Vector Containing Fusion of cenC CBD Gene Fragment and the *C. fimi* Endoglucanase A (cenA) Gene Fragment and Characterization of the Fusion Protein Construction of the Vector Plasmid pTZ-JC2 (see FIG. 10A) was digested to completion with SmaI and HindIII. The 3.9 kbp fragment was recovered. Plasmid pUC18-1.6 cenA_PT (see FIG. 10B) was digested to completion with HpaI and HindIII and the 1.1 kbp fragment was recovered. The 3.9 and 1.1 kbp fragments were than ligated to give pTZ-JC13 (see FIG. 10C). This vector is used to transform *E. coli* JM101.

Enzymatic characterization of the fusion protein

The expression product (fusion protein) encoded by pTZ-JC13 is characterized for its catalytic activity on Avicel, bacterial microcrystalline cellulose (BMCC) and phosphoric acid swollen cellulose (PASC) compared to the original CenA and its isolated catalytic domain p30. Specific activity is determined from the amount of soluble reducing sugar produced from a fixed amount of substrate under fixed assay conditions. The reducing sugar is measured by a calorimetric assay and determined using a glucose standard. The concentration of polypeptides is determined by the binding of Coomassie Brilliant Blue G-250 (Gilkes et al. (1988) *J. Biol. Chem.* 263:10401–10407).

Figure 12A:
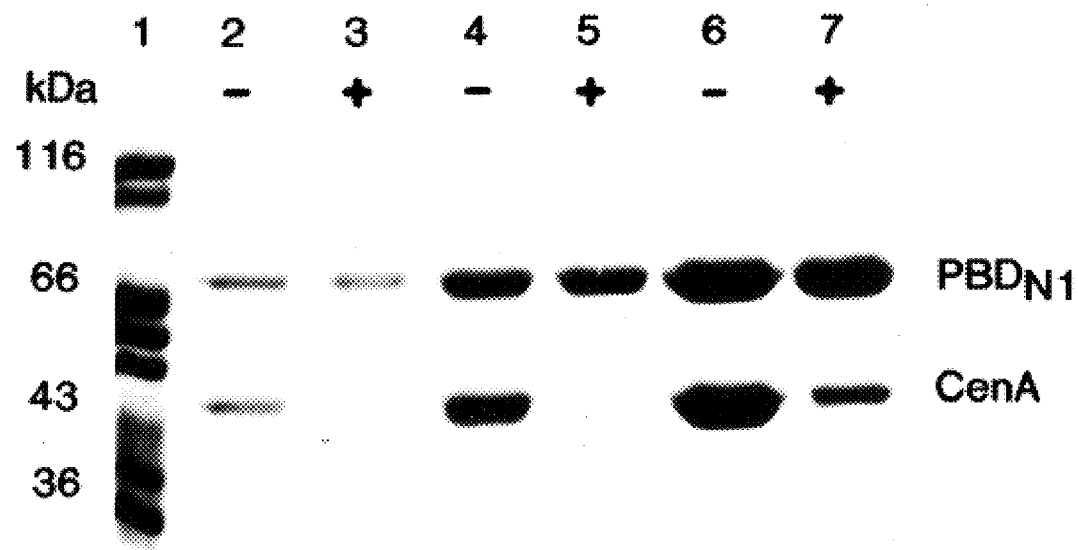
FIGS. 12A and 12B show the results of separation of CenA and $PBD_{N1}$-CenA by differential adsorption to cellulose followed by analysis of unadsorbed polypeptides using SDS-PAGE.
Figure 12B:
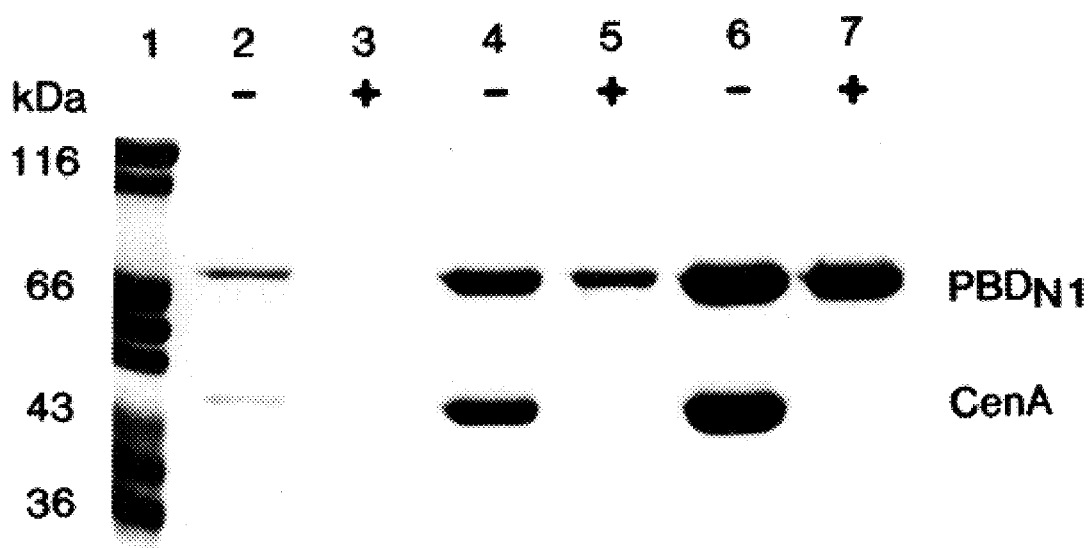

Evaluation of the susceptibility of the fusion protein to proteolytic degradation A major consideration in the use of fusion proteins is the stability of the polypeptides under a variety of conditions, including resistance against proteolytic degradation. The sensitivity of the fusion protein to proteolytic degradation in the absence of a linker sequence was evaluated with *C. fimi* protease. Cleavage of the fusion proteins with *C. fimi* protease was monitored by SDS-PAGE (see FIG. 12). The stability of the fusion protein was compared relative to the stability of CenA. The protease concentration and the proteolysis conditions were varied to optimize the results.

Evaluation of the binding characteristics of the fusion protein; differential adsorption analysis To define the affinity of the PBD-fusion proteins for different cellulose allomorphs, binding to various cellulosic matrixes can simply be evaluated by SDS-PAGE analysis of bound fractions. This analysis has shown that $PBD_{N1}$ binds to amorphous cellulose (PASC) but does not bind to crystalline cellulose (BMCC). The $CBD_{CenA}$ on the other hand has affinity for both cellulosic materials. These different binding characteristics offer the possibility for selective removal of one component in the presence of the other. In the first step BMCC is added to remove CenA. The PBD-fusion protein, left in solution after the first step, was then removed by adsorption to PASC (see FIG. 12). The concentration of the various protein components relative to the cellulose concentration was varied widely during the assay to evaluate the effect of non-saturating, saturating and over-saturating the cellulose.

This selective removal or binding of the different components has important implication for the use in processing and purification of fusion proteins. One such process could involve the proteolytic removal of the PBD from the fusion protein while bound to the polysaccharide using a CBD-protease to liberate the compound of interest. The protease is then be removed by virtue of its binding to cellulose (e.g., BMCC) leaving a pure compound.

Example 7

Production and Properties of a Bifunctional Fusion Protein that Mediates Separation of Vero Cells Using Oligosaccharide-polymer Based Affinity Phase Partitioning Bacterial Strains, Cell Lines, and Growth Conditions Chemicals were of analytical of HPLC grade. Recombinant DNA experiments were performed in *E. coli* JM 101 grown at 37° C. in LB medium supplemented with ampicillin (Boehringer Mannheim GmbH, Mannheim, Germany) at 100 μg/mL. High-level expression studies and large scale protein production were carried out in *E. coli* R1360 grown at 37° C. in TYP medium (16 g tryptone, 16 g yeast extract, 5 g NaCl, 2.5 g $K_2HPO_4$ per liter) supplemented with ampicillin (100 μg/mL). Bacterial medium components were from Difco Laboratories (Detroit, Mich.). Shaker speed for shaker flask cultures was set at 250 rpm. Cultures were induced with isopropyl-D-thiogalactoside (IPTG, Sigma Chemical Co., St. Louis, Mo.) at 0.15 mM. Vero (African green monkey, kidney-ATCC CCL 81) cells used in attachment studies were maintained in T flasks, in DMEM or DMEM/F12 medium (Gibco BRL, Gaithersburg, Md.) supplemented with 10% NCS (Gibco BRL), at 37° C., and 5% $CO_2$.

Recombinant DNA Techniques

All recombinant DNA work was carried out as described previously (Sambrook (1989) supra.). Double-stranded DNA was prepared by the alkaline-lysis method. DNA restriction and modification enzymes were used according to the manufacturer's recommendations. DNA fragments were separated by agarose gel electrophoresis. Large DNA fragments were isolated using GeneClean™ (Bio101, La Jolla, Calif.). Small DNA fragments (less than 100 bp) were isolated by the liquid nitrogen method. Frozen competent *E. coli* cells were used for all transformations. Oligodeoxynucleotides were synthesized with an ABI 380A DNA synthesizer (Applied Biosystems, Foster City, Calif.) and purified by C18 cartridge Chromatography. Annealing of oligodeoxynucleotides was performed at 74° C. for 10 min in sequencing buffer (40 mM Tris-HCl or pH 7.5, 20 MM $MgCl_2$, 50 mM NaCl), followed by slow cooling at 4° C. DNA was sequenced by the dideoxy chain terminating method using modified $T_7$ DNA polymerase (Sanger et al., *Proc. Nat'l Acad. Sci. USA* (1977) 74:5463–5467).

Polypeptide Analysis

Polypeptides were resolved by sodium dodecyl sulfate polyacrylamide gel electrophoresis (SDS-PAGE). The gels were stained with Coomassie Brilliant Blue R250 (BioRad, Richmond, Calif.); bands were quantified using a scanning densitometer (Computing Densitometer, Molecular Dynamics, Sunnyvale, Calif.) equipped with ImageQuant™ software. Pure $CBP^{N1}$/RGD standards were included with each set of gels. Concentrations of pure preparations of $CBP^{N1}$/RGD were determined by absorbance at 280 nm using the extinction coefficient determined for pure CBD/RGD (Scopes, *Anal. Biochem.* (1974) 59:277–282). Western blotting was performed using rabbit anti-CenA serum as primary antibody and goat anti-rabbit serum conjugated to horseradish peroxidase (Gibco BRL) as secondary antibody.

Oligosaccharide Binding Assay

This was performed as described in Example 2.

Figure 17:
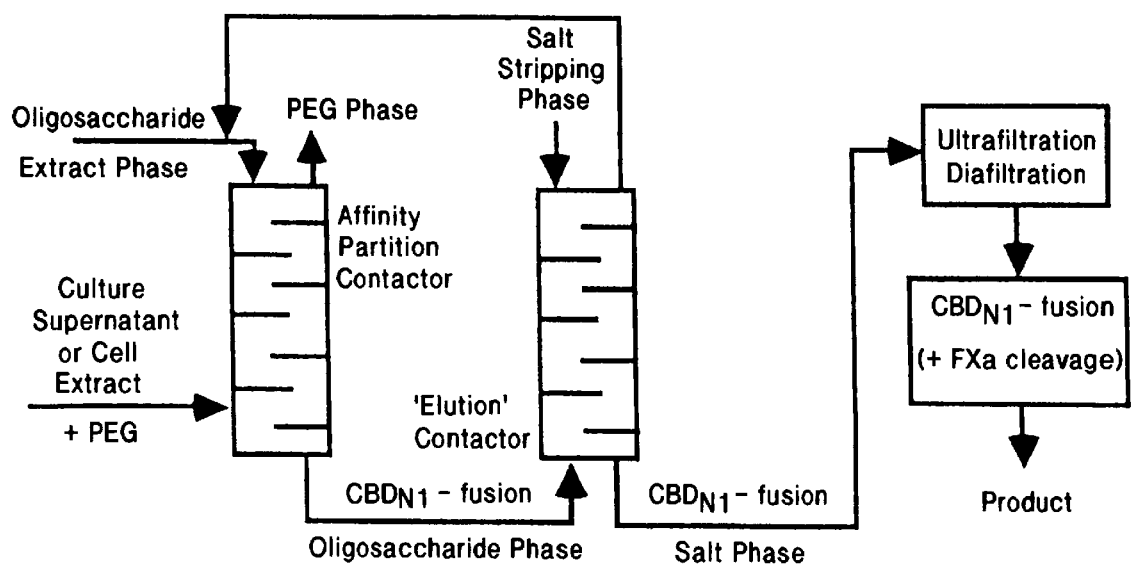
FIG. 17 shows a schematic of an affinity partition system based on novel $CBD_{N1}$-fusion technology. After a diafiltration step to remove excess salt, the target protein, when necessary, can be recovered from the fusion construct by cleavage at an IQGR-specific recognition site for Factor $X_a$ inserted at the −1 position relative to the target protein (See Assouline et al., (1993) *Protein Eng.*, 7:787) for suitable expression systems for Factor $X_a$ and for Factor $X_a$-CBD fusion proteins. Direct recovery of the target protein by Factor $X_a$ cleavage directly after the affinity partition step can be used to simplify the process.

Large-Scale Production and Purification of $CBP_{N1}$/RGD $CBD_{N1}$ is produced as described in Wierzba et al., *Biotechnol. and Bioeng.* (1995) 47:147–154, except that the coding sequence for $CBD_{N1}$ replaces the coding sequence for the cellutese binding domain (CBD) of allulomanase fimi endoglucanase A (CenA) in the R1360/pTZ18U-CBD/RGD construct. *E. coli* containing the construct are grown at 37° C. in a 12-L fermentor (Chemap AG, Volketswil, Switzerland) in TYP medium supplemented with ampicillin (100 μg/mL), and IPTG (0.15 mM). Cells are separated from the culture medium by centrifugation at 31,000 g (Sharples-Stokes Division, Pennwalt Corp., Warminster, Pa.). $CBD_{N1}$/RGD in the culture medium and in the cellular fraction is purified separately using affinity-phase partitioning using mixtures of HEC and plucronic pios as described in Example 4. Culture medium is filtered through a GF/C glass fiber filter (Whatman International, Maidstone, UK) to remove cell debris. The culture medium is added to the phase separation system. According to the methodology for other aqueous two-phase partition systems (e.g., Joshi et al., *Bioseparations,* (1990) 11:311) with the important difference that the separation is greatly enhanced by binding of the $CBD_{N1}$ fusion to the HEC. FIG. 17 is a schematic of the system, where affinity extraction of the $CBD_{N1}$-fusion protein from a culture supernatant or a cell extract occurs in either a commercial Graesser-type contractor (employed in most large-scale partitioning systems) or a mixer-settler batter (Haynes, PhD Thesis, University of California at Berkeley (1991)). The carbohydrate-rich extract phase containing the $CBD_{N1}$-fusion protein is pumped to a second mixer-settler batter for back extraction of the product, while the poly(oxy-ether)-rich phase is stripped with an incompatible sale and then recycled to the affinity extractor (Haynes et al., *AIChE J.,* (1991) 37:1401). Addition of sufficient salt, usually a sulfate or citrate salt, to a carbohydrate-rich extract phase containing a bound target protein results in phase separation (see Walter et al., *Partitioning in Aqueous Two-Phase Systems,* Academic Press (1985)). The 2-M and higher salt concentrations required for phase separation often leads to dissociation of the ligand-protein complex and thus, a simple means of product recovery. The strongly exothermic binding between $CBD_{N1}$ and HEC indicates that dissociation can also be achieved through either a modest increase in temperature or addition of a hydrogen-bond disrupting cosolvent. Excess salt is removed by diafiltration or other desatting methodology. The suspension is stirred gently at 4° C. overnight. The eluate is concentrated and exchanged with $dH_2O$ (to less than 50 rM GdmC1) by ultrafiltration using a 1-dD cutoff membrane (Amicon Division, W.R. Grace & Co., Beverly, Mass.). The $CBD_{N1}$/RGD solution (5 to 12 mg/mL) is filter sterilized (0.2 $\mu$m) and stored at −20° C.

E. coli cells are washed with 50 mM potassium phosphate buffer (pH 7.0), resuspended in 150 mL of the same buffer supplemented with 3 mM EDTA, and ruptured in a 50-mL French pressure cell (SLM Instruments, Urbana, Ill.). Phenylmethylsulfonylfluoride (1 mM) and pepstatin A (1 $\mu$M) are added to the cell extract to minimize proteolysis. Cellular debris is removed by centrifugation at 17,400 g for 30 min at 4° C. Streptomycin sulfate (Sigma) is added to the supernatant (1.5 % w/v). After incubation overnight at 4° C., the precipitate is collected by centrifugation at 17,400 g for 30 min at 4° C. The supernatant is added to the affinity partition system and the $CBD_{N1}$/RGD is purified as described above for the culture broth.

Cell Separation Assay

Cells are detached from culture dishes with trypsin and EDTA, washed once with DMEM medium containing 0.01% soybean Trypsin inhibitor (Sigma), and twice with DMEM medium without the inhibitor. To a total of $4'10^6$ washed cells is $CBD_{N1}$ in serum-free culture medium. After incubation for 1 h at 37° C., the cells with $CBD_{N1}$/RGD bound are added to the affinity phase partitioning system. After separation of the HEC phase, trypsin is added to release the cells from the HEC and the cells are collected by centrifugation. Viability of the cells is assessed using trypan blue exclusion.

Example 8

Figure 13A:
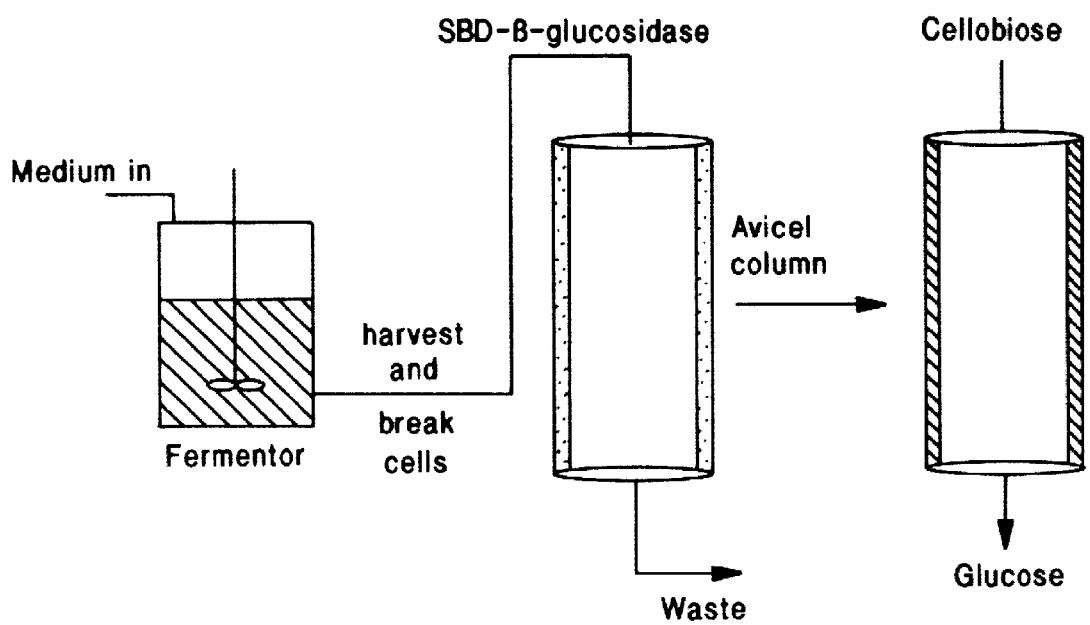
FIGS. 13A and 13B are schematic diagrams for immobilization and use of a fusion protein.
Figure 13B:
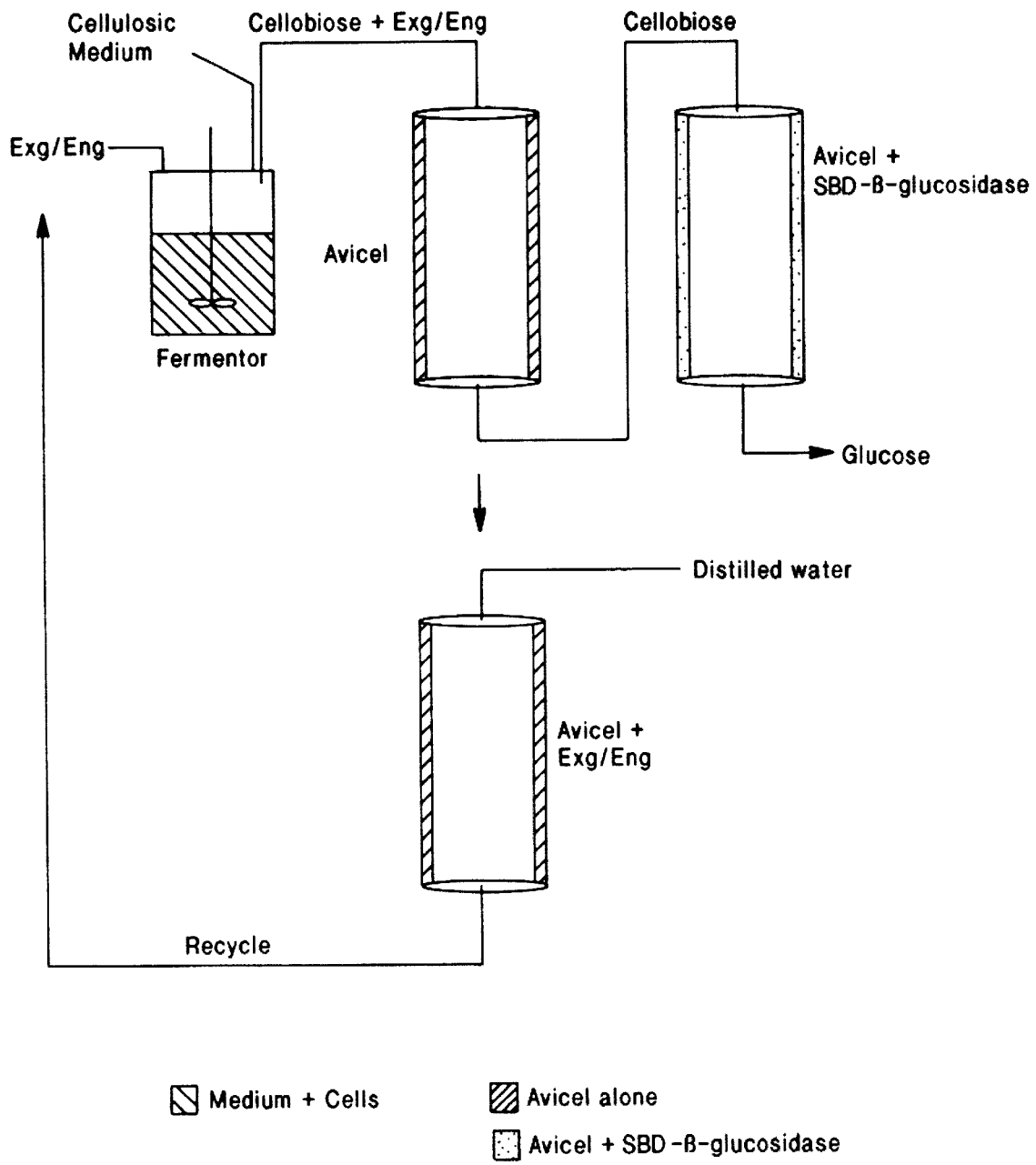

Production of Glucose from Cellobiose Using β-glucosidase Fusion Protein Immobilized on Avicel This procedure uses an endoglucanase-exoglucanase coincubation with subsequent channeling of the resulting cellobiose mixture into an Avicel column upon which β-glucosidase is immobilized (see FIG. 13B). The method is as follows. In a fermentation vessel a suitable proportion of both endoglucanase and exoglucanase is added to a medium containing the cellulosic material to be degraded. The enzymes are allowed to react for a fixed period of time to produce cellobiose which is solubilized in the medium. The whole spent medium together with the enzyme is first passed through an Avicel column which immobilizes and concentrates both the endoglucanase and the exoglucanase. The eluent containing the cellobiose is channeled to a second Avicel column with immobilized β-glucosidase $PBD_{Cex}$ fusion protein which then hydrolyses the cellobiose into glucose units. The endoglucanase and the exoglucanase are regenerated from the first column by elution. Both columns can be reused several times for purification and enzymatic conversion.

Example 9

Preparation of $CBD_{N1}$-Alkaline Phosphatase Fusion Protein Expression Cassette TNphoA is a derivative of transposon Tn5 containing the E. coli alkaline phosphatase gene, phoA, minus its signal sequence ('phoA). Transpositional insertion into an expressed gene in the correct reading frame creates a PhoA fusion protein. If the target gene contains protein export signals, these can direct the secretion of the fusion protein. This secretion is detectable by alkaline phosphatase activity, which is present only when the enzyme has been secreted to the periplasm. TnphoA is used to create phoA gene fusions with the C. fimi $CBD_{N1}$ coding sequence in a plasmid having a multiple cloning site. A gene encoding a protein of interest can be cloned into a multiple cloning site (mcs) and expressed as a fusion protein. The gene product is purified by affinity phase partitioning in HEC-Pluronic IOS $CBD_{N1}$.

Preparation and Analysis of Gene Fusions

Figure 6:
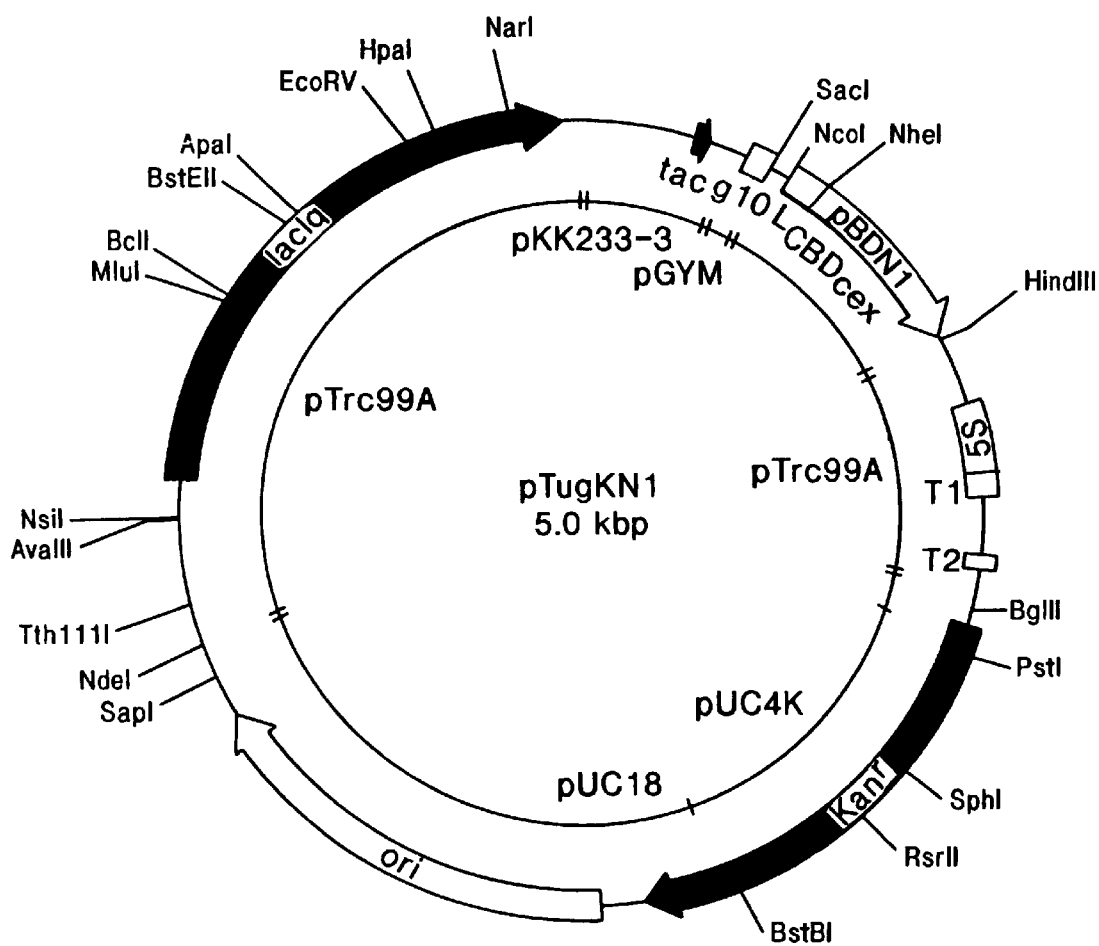
FIG. 6 shows the pTugKN1 vector. The pTugKN1 vector is derived from the pTugA vectors by replacing the selective marker for ampicillin resistance (β-lactamase encoding sequence) with the selective marker for kanamycin resistance. The sequence encoding the leader peptide of the endoglucanase A (CenA) of *C. fimi* was replaced with the encoding sequence for the leader peptide of the exoglucanase (Cex) from *C. fimi* (Ong et al. *Biotechnol. Bioeng.* (1993) 42:401–409).

Transpositional mutagenesis with TnphoA is used to create gene fusions with $CBD_{N1}$. The plasmid containing $CBD_{N1}$ is $pTugK_{N1}$ (see FIGS. 5 and 6).

The transposition event is mediated by infection of E. coli CC118 ($pTugK_{N1}$) with a defective lambda phage containing the transposon, λTnphoA-1 (Gutierrez et al., J. Mol. Biol. (1987) 195:289–297). E. coli CC118 contains a deletion in the phoA gene. Transpositional insertion into the $CBD_{N1}$ coding sequence in-frame with the $CBD_{N1}$ creates a $CBD_{N1}$-PhoA fusion protein targeted for the extracellular medium. Colonies selected for kanamycin (transposon-derived) and ampicillin resistance are screened for alkaline phosphatase activity on the chromogenic substrate 5-bromo-4-chloro-3-indolyl phosphate (XP). Plasmid DNA from PhoA+ colonies are retransformed, and selected and screened as above. PhoA+ colonies are screened for endo-glucanase activity on carboxymethyl-cellulose (CMC) plates stained with Congo red (Greenwood et al., FEBS Letters (1984) 2:259–263). The desired phenotype is PhoA+, EngA−, and resistant to ampicillin and kanamycin.

Plasmid DNA is isolated from PhoA+, EngA− colonies and analyzed by restriction digestion and agarose gel electrophoresis for colonies which have TnphoA insertions in $CBD_{N1}$ in the correct orientation. Some of these clones can have out-of-frame insertions, a possibility that becomes evident when looking at the protein products of the fusions. The $CBD_{N1}$-PhoA fusion proteins are analyzed for binding to soluble oligosaccharides such as HEC. The exact insertion position of TnphoA is determined by DNA sequencing using the chain-termination method.

Purification of Fusion Protein

Cleared E. coli cell extracts containing the fusion protein are applied to an HEC-pluranic 105 affinity phase partitioning system in a buffer which promotes binding of the fusion protein to the HEC polymer. After separation of the HEC phase from the pluranic 105 phase, the fusion protein is dissociated by increasing the temperature and collecting the fusion protein. Collected fractions are assayed for alkaline phosphatase activity, and the enzyme peak further purified by ion exchange or gel filtration chromatography. Purification conditions are varied to optimize the recovery of alkaline phosphatase activity.

Figure 14:
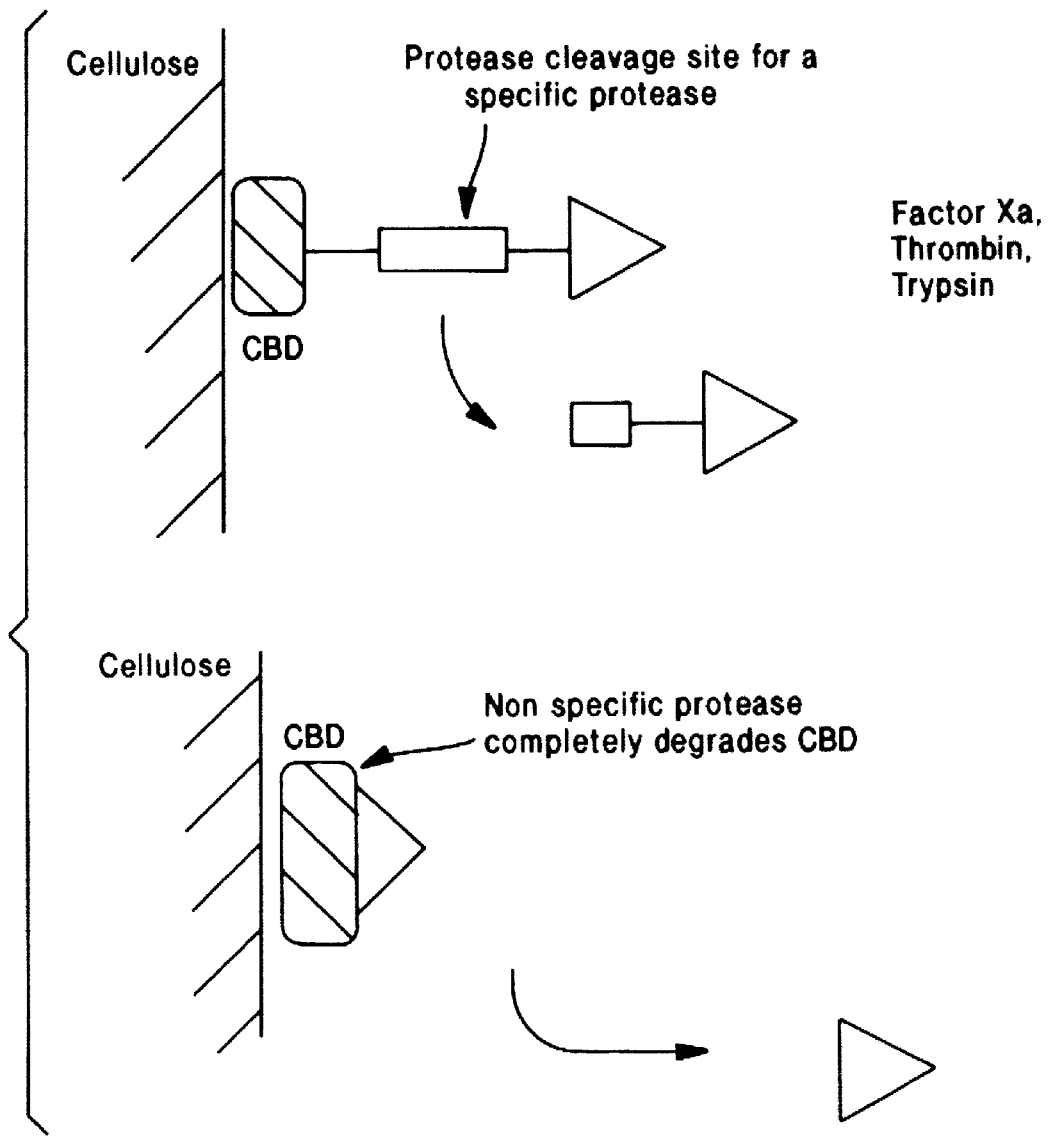
FIG. 14 shows two removable label compositions and means for enzymatically debinding the removable label from a cellulose substrate: an arrow indicates a chemical moiety, an open box indicates a protease cleavage site for a specific protease, and a cross-hatched box indicates a cellulose-binding domain.

The parameters (± accumulated standard error) were calculated from adsorption data plotted in double reciprocal form. The values for $K_a$ and $\alpha$ were calculated using [No]=101 $\mu$mol lattice residues cellulose$^{-1}$, as detailed in Example 3, C. Adsorption and relative affinity of $PBP_{Cex}$ to cellulose, including Avicel, BMCC and regenerated cellulose (RC), and of chitin are shown in FIGS. 15 and 16 of U.S. Ser. No. 5,340,731. FIG. 17 of U.S. Ser. No. 5,340,731 shows the influence of adding detergents on the binding of $CEB_{Cex}$ to the compositions of the subject invention comprising hybrid proteins in which at least the PBP of a polysaccharidase is coupled to a ligand of interest such as a protein or a chemical moiety, for example a dye or pigment. Examples of enzymatically debinding two different removable label recompositions from cellulose are shown in FIG. 14 (above).

Example 10

Single Thermoseparating Polymer Systems

A class of affinity concentration and separation systems which use a single thermoseparating polysaccharide for which $CBD_{N1}$ or another soluble polysaccharide binding domain has affinity. Members of this family of polysaccharides include methyl cellulose, ethyl hydroxyethyl cellulose, propyl hydroxyethyll cellulose, and hydroxypropyl methyl cellulose. These systems can be used to either bind and separate fusion/hybrid proteins containing a soluble oligosaccharide binding domain which are excreted during culture to the culture supernatant, or to bind and separate intracellular fusion/hybrid proteins containing a soluble oligosaccharide binding domain following cell lysis, osmotic shock, etc. In either system, the process is as follows: A thermoseparating polysaccharide is added to a culture supernatant or lysate containing exposed fusion protein at a temperature below the current point temperature. The thermoseparating polysaccharide and the culture supernatant or lysate is mixed and the temperature is raised slowly until it reaches a point above the current point temperature for the polysaccharide. Upon formation of a polymer-rich phase in the remaining solution, the polymer-rich phase can be recovered and fusion protein eluted from the polysaccharide. The remaining solution with all remaining solutes can then be discarded.

The process is divided into four steps: addition of a thermoseparating polymer to an aqueous solution containing an oligosaccharide binding protein or any fusion protein containing an oligosaccharide binding protein and contact and binding of the polymer to the said protein; slow elevation of the temperature under mixing conditions to a temperature above the CPT; elimination of mixing at a temperature above the CPT to facilitate separation of the water-rich and polymer-rich phase (which can be accomplished by either gravitational settling or enhanced by centrifugation; and recovery of the polymer-rich phase (which contains the target protein) and elution of the target oligosaccharide binding protein or the fusion protein containing an oligosaccharide binding protein.

Example 11

Affinity Aqueous Two-Phase Systems Containing One or More Thermoseparating Polymers Aqueous two-phase systems which contain one or more thermoseparating polymers which have an affinity for $CBD_{N1}$ have been compiled (See Table below). These systems allow for a high-affinity separation to the phase containing the polymer to which the domain binds followed by a simple method for recovering and recycling the polymer.

Four different cellulose-based polymers capable of binding $CBD_{N1}$ and other oligosaccharide binding proteins were used in conjunction with two other non-cellulose polymers to form a number of novel aqueous two-phase systems. The properties of the aqueous two-phase systems formed are discussed below.

Pluronic—Klucel Systems

Eight different grades of Pluronics were used with three grades of Klucel. The Pluronics used included F68, F77, F108, P84, P103, P104, P105, and P123. The grades of Klucel used were Klucel H, 1 and M.

Pluronic F68—Klucel H: Two-phase systems are formed from solutions containing at least 10% (total weight percent) of each polymer.

Pluronic F68—Klucel L: Two-phase systems are formed from solutions containing at least 13% (total weight percent) of each polymer.

Pluronic F68—Klucel M: Phase separation is observed for polymer concentrations greater than 12% (w/w).

Pluronic F77—Klucel H: Phase separation is observed for solutions in the range of 9% of each polymer. The upper phase is clear while the lower phase is cloudy.

Pluronic F77—Klucel L: Phase separation is observed for solutions with concentrations in the range of 10% (w/w) of each polymer.

Pluronic F77—Klucel M: Two-phase systems are formed from solutions containing at least 10% (total weight percent) of each polymer.

Pluronic F108—Klucel H: Two-phase systems are formed from solutions containing at least 10% (total weight percent) of each polymer.

Pluronic F108—Klucel L: Two-phase systems are formed from solutions containing at least 10% (total weight percent) of each polymer.

Pluronic F108—Klucel M: Two-phase systems are formed from solutions containing at least 9% (total weight percent) of each polymer.

Pluronic P103—Klucel H: Separation is observed for concentrations around 6.5% Pluronic and 7.1% Klucel.

Pluronic P104—Klucel H: Separation is observed for solutions of concentrations of 4.1% Pluronic and 3.8% Klucel.

Pluronic P105—Klucel H Phase separation is observed for solutions of concentrations of 4.5% Pluronic and 2.8% Klucel. Two-phase systems at low concentrations are not viscous.

Pluronic P105—Klucel L: Separation occurs for concentrations in the range of 5.0% Pluronic and 3.5% Klucel. The two-phase solutions in this range are not viscous. The lower phase thermoseparates at temperatures above 40° C.

Pluronic P105 Klucel M: Phase separation is observed for concentrations with as low as 3.9% Pluronic and 2.5% Klucel. The lower phase becomes viscous and cloudy at temperatures above 38° C.

Pluronic P123—Klucel H: Two-phase sytems are formed at concentrations of 5.6% Pluronic and 4.0% Klucel.

Dextran—Natrosol Systems

Three grades of Dextran were used with three grades of Natrosol to form a novel set of aqueous two-phase systems. The grades of Dextran included grades of T40, T70 and T500 while Natrosol grades included 250 HR, 250 LR and 250 MR.

Dextran T40—Natrosol 250 LR: Aqueous two-phase systems are formed from solutions of concentrations in the range of 10% for each polymer.

Dextran T70—Natrosol 250 LR: Aqueous two-phase systems are formed from solutions of about 5.2% Dextran and 5.0% Natrosol.

Dextran T500—Natrosol 250LR: Aqueous two-phase systems are formed from solutions of 5.3% for both polymers.

Pluronic—Dextran Systems

Four grades of Dextran were used in conjunction with four grades of Pluronic to form a novel set of aqueous two-phase systems useful for the invention. The grades of Dextran used included T40, T500 and T2000. The Pluronics used included F68, F77, F108 and P105. Excellent phase separation properties were observed for most of the combinations of polymers tested in terms of low polymer concentrations and low viscosity.

Pluronic F68—Dextran T40: Phase separation is observed for concentrations around 9.0% for each polymer. The two-phase system is both clear and not very viscous at these concentrations.

Pluronic F68—Dextran T70: Phase separation is observed for concentrations of Pluronic and Dextran of 7.0% and 5.9% respectively.

Pluronic F68—Dextran T500: Aqueous two-phase systems are formed at concentrations around 6.3% for each polymer.

Pluronic P68—Dextran T2000: Aqueous two-phase systems are formed at concentrations around 9.0% for each polymer.

Pluronic F77—Dextran T40: Aqueous two-phase systems are formed at concentrations of 10.0% Pluronic and 9.2% Dextran.

Pluronic F77—Dextran T70: Phase separation occurs for solutions of concentrations of about 8.2% for each polymer.

Pluronic F77—Dextran T500: Aqueous two-phase systems are formed at concentrations of 7.0% for both polymers.

Pluronic F77—Dextran T2000: Phase separation is observed at a concentration of 10.7% for both polymers.

Pluronic F108—Dextran T40: Aqueous two-phase systems are formed at concentrations around 7.0% for each polymer.

Pluronic F108—Dextran T70: Aqueous two-phase systems are formed at concentrations in the range of 7.0%.

Pluronic F108—Dextran T500: Phase separation occurs at a concentration of 3.9% Pluronic and 3.4% Dextran.

Pluronic F108—Dextran T2000: Aqueous two-phase systems are formed at concentrations in the range of 3.4% Pluronic and 3.9% Dextran.

Pluronic P105—Dextran T40: Aqueous two-phase systems are formed at concentrations in the range of 8.0% for each polymer.

Pluronic P105—Dextran T70: Aqueous two-phase systems are formed at Pluronic and Dextran concentrations of 6.3%.

Pluronic P105—Dextran T500: Separation occurs at concentrations slightly lower than 6.0% for each polymer.

Pluronic P105—Dextran T2000: Phase separation occurs at a concentration in the range of 6.0% for each polymer.

Klucel—Dextran Systems

Three grades of Klucel were used in conjunction with four grades of Dextran to form a novel set of aqueous two-phase systems. The grades of Klucel used included Klucel H, L and M. The grades of Dextran used included Dextran T40, T70, T500 and T2000.

Klucel H—Dextran T40: Aqueous two-phase systems are formed at concentrations of Klucel and Dextran of 6.8% and 8.3% respectively.

Klucel H—Dextran T70: Aqueous two-phase systems are formed at concentrations of 6.8% for each polymer.

Klucel H—Dextran T500: Phase separation occurs at concentrations slightly greater than 3.0%.

Klucel H—Dextran T2000: Phase separation is observed for concentrations in the range of 3.2%.

Klucel L—Dextran T40: Phase separation is observed for solutions of concentrations greater than 4.0 %.

Klucel L—Dextran T70: Aqueous two-phase systems are formed at concentrations of 3.6% for each polymer.

Klucel L—Dextran T500: Separation is observed at concentrations of 3.9%.

Klucel L—Dextran T2000: Phase separation is observed for concentrations of 3.5% Klucel and 3.1% Dextran.

Klucel M—Dextran T40: Aqueous two-phase systems are formed at concentrations of slightly greater than 3.1%.

Klucel M—Dextran T70: Phase separation is observed for concentrations in the range of 3.5%.

Klucel M—Dextran T500: Phase separation is observed for polymer concentrations of 3.5%.

Klucel M—Dextran T2000: Aqueous two-phase systems are formed at concentrations of lower than 4.0%.

HPMC—Dextran Systems

Sigma HPMC was used with five different grades of Dextran to form a novel set of aqueous two-phase systems. The grades of Dextran used included Dextran T40, T70, T500, T2000, and a Sodium Dextran Sulfate.

HPMC—Dextran T40: Phase separation is observed for concentrations less than 3.0% for each polymer.

HPMC—Dextran T70: Separation is observed for polymer concentrations of 3.8% HPMC and 4.6% Dextran.

HPMC—Dextran T500: Phase separation occurs for solutions of concentrations less than 3.4%.

HPMC—Dextran T2000: Separation occurs for concentrations close to 4.0%.

HPMC—Sodium Dextran Sulfate: Separation occurs from concentrations of 2.9% HPMC and 4.1% Sodium Dextran Sulfate.

HPMC—Pluronic Systems

Sigma HPMC was used with five grades of Pluronic to form a novel set of aqueous two-phase systems. The Pluronic comes from the P-series and include Pluronic P84, P103, P104, P105 and P123.

HPMC—Pluronic P84: Phase separation is observed for concentrations of 6.3% HPMC and 7.8% Pluronic. At this concentration, the upper phase is clear and very small indicating that this solution may be close to the phase boundary.

HPMC—Pluronic P103: Aqueous two-phase systems are formed at concentrations less than 4.0%.

HPMC—Pluronic P104: Separation occurs for solutions of concentrations in the range of 3.6%.

HPMC—Pluronic P105: Phase separation is observed for polymer concentrations in the range of 5.5%.

HPMC—Pluronic P123: Phase separation occurs at a concentration of 5.5% HPMC and 6.4% Pluronic.

Example 12

Affinity Electrophoresis Analysis of Interaction Between Cellulose-Based Polymers and CBD Affinity electrophoresis analysis was used on the four cellulose-based polymers in order to determine any interactions between the molecule and the N-terminal of the Cellulose-Binding Domain ($CBD_{N1}$) of *Cellulomonas fimi*

CenC. $CBD_{N1}$ and $CBD_{N1N2}$ were tested separately on all four cellulose-based polymers. Bovine serum albumin (BSA), which does not bind to cellulose molecules, was used as a control. The results are summarized below.

Klucel (HPC)

Strong binding interactions between Klucel H and Klucel L with $CBD_{N1}$ and $CBD_{N1N2}$ were observed at pH7 resulting in total loss of migration on the gel. (See FIG. 9).

Natrosol (HEC)

Strong binding of Natrosol with $CBD_{N1}$ and $CBD_{N1N2}$ was observed (See FIG. 9).

Bermocoll E (EHEC)

Binding interactions were studied for the two grades of Bermocoll E with the $CBD_{N1}$ and $CBD_{N1N2}$. Both polymers bind strongly to either $CBD_{N1}$ and $CBD_{N1N2}$ as measured by the electrophoresis assay.

Hydroxypropylmethyl Cellulose (HPMC)

HPMC binds strongly to either $CBD_{N1}$ or $CBD_{N1N2}$ as measured by the electrophoresis assay.

Current affinity partition systems are limited in their capacity and resolving power by low ligand densities which result from the presence of only one or two ligands per polymer chain. Since polymer concentrations are usually less than 15 wt %, affinity partition systems with a 1:1 or 2:1 ligand to polymer stoichiometry usually yield target protein separation factors (relative to those of the contaminants) between 5 and 50. These separation factors are more than sufficient for product concentration, but do not always provide a desired product purity in a cost-effective, one- or two-stage extraction process. Classic affinity partition systems are also limited by the expense of the chemistry needed to produce the polymerligand conjugates. These cost and capacity limitations can be eliminated if the monomeric unit of one of the phase-forming polymers served as the affinity ligand. The exquisitely selective binding of $CBD_{N1}$ to a variety of water-soluble cellulosic substrates offers new, cost-effective, highly-flexible affinity partition system for continuous purification or recombinant proteins. Genetic linkage of $CBD_{N1}$ to a target protein or peptide results in a fusion which binds strongly to water-soluble carbohydrates in the presence of centimolar quantities of electrolyte and retains the biological activity of the fusion partner.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A two-phase partition system for affinity separation comprising:
    as a first component a phase-forming oligosaccharide polymer to which a polysaccharide binding peptide binds with a Ka of $10^3$ M to $10^7$ M and as a second component a phase separation inducing agent selected from the group consisting of a polyethylene glycol polymer, a dextran, a copolymer of ethylene oxide and propylene oxide, and a salt at a concentration of at least 3 M, wherein said first and second components are each present in an amount sufficient to induce phase separation upon mixing of said first component and said second component, wherein said first component is selected from the group consisting of methyl cellulose, and ethylhydrokyethyl cellulose.

2. A composition comprising:
    a polypeptide which comprises a non-catalytic polysaccharide binding peptide bound to (1) a phase-forming oligosaccharide polymer and (2) a cell having a carbohydrate residue on its surface to which said polysaccharide binding peptide binds, wherein said composition is obtained by the method of contacting said polysaccharide binding peptide with said cell to form a complex with said cell and contacting said complex with a two-phase partition system which comprises as a first phase a phase-forming oligosaccharide polymer to which said polysaccharide binding peptide binds with a Ka of $10^3$ M to $10^7$ M, and as a second phase a phase separation inducing agent selected from the group consisting of a polyethylene glycol polymer, a dextran, and a copolymer of ethylene oxide and propylene oxide, and a salt at a concentration of at least 3 M, whereby said complex partitions into said first phase by binding to said phase-forming oligosaccharide polymer; and recovering said first phase, whereby said composition is obtained.

3. The composition according to claim 2, wherein said phase-forming oligosaccharide polymer is a β-1,4-glucan.

4. The composition according to claim 3, wherein said β-1,4-glucan is a cellulose.

5. The composition according to claim 3, wherein said β-glucan is obtainable from a cereal.

6. The composition according to claim 5, wherein said cereal is oat or barley.

7. The composition according to claim 2, wherein said polysaccharide binding peptide is derived from a polysaccharide binding domain of a polysaccharidase.

8. The composition according to claim 7, wherein said polysaccharidase is a cellulase.

9. A composition comprising:
    a polypeptide which comprises a non-catalytic polysaccharide binding peptide bound to (1) a phase-forming oligosaccharide polymer and (2) a cell having a carbohydrate residue on its surface to which said polysaccharide binding peptide binds, wherein said composition is obtained by the method of contacting said polysaccharide binding peptide with said cell to form a complex with said cell and contacting said complex with a two-phase partition system which comprises as a first phase a phase-forming oligosaccharide polymer selected from the group consisting of hydroxyethyl cellulose, carboxymethyl cellulose, methyl cellulose, ethylhydroxyethyl cellulose and hydroxypropyl cellulose, and as a second phase a phase separation inducing agent selected from the group consisting of a polyethylene glycol polymer, a dextran, and a copolymer of ethylene oxide and propylene oxide, and a salt at a concentration of at least 3 M, whereby said complex partitions into said first phase by binding to said phase-forming oligosaccharide polymer; and recovering said first phase, whereby said composition is obtained.

10. The composition according to claim 9, wherein said polysaccharide binding peptide is derived from *C. fimi* endoglucanse C.

11. The composition according to claim 10, wherein said polysaccharide binding peptide is $CBD_{N1}$.

12. The composition according to claim 9, wherein said phase separation inducing agent is selected from the group consisting of a polyethylene glycol polymer, a dextran, and a copolymer of ethylene oxide and propylene oxide.

13. A composition comprising:
   a fusion polypeptide which comprises a non-catalytic polysaccharide binding peptide and a ligand bound to (1) a phase-forming oligosaccharide polymer and (2) a cell having a receptor for said ligand on its surface to which said ligand binds, wherein said composition is obtained by the method of contacting said fusion polypeptide with said cell to form a complex with said cell and contacting said complex with a two-phase partition system which comprises as a first phase a phase-forming oligosaccharide polymer to which said polysaccharide binding peptide binds with a Ka of $10^3$ M to $10^7$ M, and as a second phase a phase separation inducing agent selected from the group consisting of a polyethylene glycol polymer, a dextran, and a copolymer of ethylene oxide and propylene oxide, and a salt at a concentration of at least 3 M, whereby said complex partitions into said first phase by binding to said phase-forming oligosaccharide polymer; and recovering said first phase, whereby said composition is obtained.

14. The composition according to claim 13, wherein said ligand is a macromolecule.

15. The composition according to claim 14, wherein said macromolecule is a protein.

16. The composition according to claim 14, wherein said macromolecule is selected from the group consisting of an enzyme, a hormone, and an antibody.

17. The composition according to claim 14, wherein said macromolecule is bound to said polysaccharide binding peptide via an amino acid sequence.

18. The composition according to claim 14, wherein said fusion polypeptide comprises a protease recognition sequence between said polysaccharide binding peptide and said macromolecule.

19. The composition according to claim 18, wherein said protease recognition sequence is heterologous to said polysaccharide binding peptide.

20. The composition according to claim 18, wherein said protease recognition sequence is a factor Xa recognition sequence.

21. The composition according to claim 18, wherein said protease recognition sequence is a non-specific protease recognition sequence.

22. A two-phase partition system for affinity separation comprising:
   as a first component a phase-forming oligosaccharide polymer to which a polysaccharide binding peptide binds with a Ka of $10^3$ M to $10^7$ M and as a second component a phase separation inducing agent selected from the group consisting of a dextran, a copolymer of ethylene oxide and propylene oxide, and a salt at a concentration of at least 3 M, wherein said first and second components are each present in an amount sufficient to induce phase separation upon mixing of said first component and said second component, wherein said first component is selected from the group consisting of hydroxyethyl cellulose, carboxymethyl cellulose, methyl cellulose, ethylhydroxyethyl cellulose and hydroxypropyl cellulose.

* * * * *

```
                           SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
         (A) LENGTH: 148 amino acids
         (B) TYPE: amino acid
         (D) TOPOLOGY: unknown (ii) MOLECULE TYPE: protein (iii) HYPOTHETICAL: no (xi) SEQUENCE DESCRIPTION: SEQ ID NO:1:

Ala Ser Pro Ile Gly Glu Gly Thr Thr Phe Asp Asp Gly Pro Glu Gly
 1               5                  10                  15

Trp Val Ala Tyr Gly Thr Asp Gly Pro Leu Asp Thr Ser Thr Gly Ala
            20                  25                  30

Leu Cys Val Ala Val Pro Ala Gly Ser Ala Gln Tyr Gly Val Gly Val
        35                  40                  45

Val Leu Asn Gly Val Ala Ile Glu Glu Gly Thr Thr Tyr Thr Leu Arg
    50                  55                  60

Tyr Thr Ala Thr Ala Ser Thr Asp Val Thr Thr Val Arg Ala Leu Val
 65                  70                  75                  80

Gly Gln Asn Gly Ala Pro Tyr Gly Thr Val Leu Asp Thr Ser Pro Ala
                85                  90                  95

Leu Thr Ser Glu Pro Arg Gln Val Thr Glu Thr Phe Thr Ala Ser Ala
               100                 105                 110
```

-continued

```
Thr Tyr Pro Ala Thr Pro Ala Asp Asp Pro Glu Gly Gln Ile Ala
            115                 120                 125

Phe Gln Leu Gly Gly Phe Ser Ala Asp Ala Trp Thr Phe Cys Leu Asp
130                 135                 140

Asp Val Ala Leu
145
```

(2) INFORMATION FOR SEQ ID NO:2:

(i) SEQUENCE CHARACTERISTICS:
        (A) LENGTH: 143 amino acids
        (B) TYPE: amino acid
        (D) TOPOLOGY: unknown (ii) MOLECULE TYPE: protein (iii) HYPOTHETICAL: no (xi) SEQUENCE DESCRIPTION: SEQ ID NO:2:

```
Val Glu Leu Leu Pro His Thr Ser Phe Ala Glu Ser Leu Gly Pro Trp
1               5                   10                  15

Ser Leu Tyr Gly Thr Ser Glu Pro Val Phe Ala Asp Gly Arg Met Cys
            20                  25                  30

Val Asp Leu Pro Gly Gly Gln Gly Asn Pro Trp Asp Ala Gly Leu Val
        35                  40                  45

Tyr Asn Gly Val Pro Val Gly Glu Gly Glu Ser Tyr Val Leu Ser Phe
    50                  55                  60

Thr Ala Ser Ala Thr Pro Asp Met Pro Pro Val Arg Val Leu Val Gly
65                  70                  75                  80

Glu Gly Gly Gly Ala Tyr Arg Thr Ala Phe Glu Gln Gly Ser Ala Pro
                85                  90                  95

Leu Thr Gly Glu Pro Ala Thr Arg Glu Tyr Ala Phe Thr Ser Asn Leu
            100                 105                 110

Thr Phe Pro Pro Asp Gly Asp Ala Pro Gly Gln Val Ala Phe His Leu
        115                 120                 125

Gly Lys Ala Gly Ala Tyr Glu Phe Cys Ile Ser Gln Val Ser Leu
    130                 135                 140
```

(2) INFORMATION FOR SEQ ID NO:3:

(i) SEQUENCE CHARACTERISTICS:
        (A) LENGTH: 155 amino acids
        (B) TYPE: amino acid
        (D) TOPOLOGY: unknown (ii) MOLECULE TYPE: protein (iii) HYPOTHETICAL: no (xi) SEQUENCE DESCRIPTION: SEQ ID NO:3:

```
Val Gly Leu Pro Trp His Val Val Glu Ser Tyr Pro Ala Lys Ala Ser
1               5                   10                  15

Phe Glu Ile Thr Ser Asp Gly Lys Tyr Lys Ile Thr Ala Gln Lys Ile
            20                  25                  30

Gly Glu Ala Gly Lys Gly Glu Arg Trp Asp Ile Gln Phe Arg His Arg
        35                  40                  45

Gly Leu Ala Leu Gln Gln Gly His Thr Tyr Thr Val Lys Phe Thr Val
    50                  55                  60

Thr Ala Ser Arg Ala Cys Lys Ile Tyr Pro Lys Ile Gly Asp Gln Gly
65                  70                  75                  80
```

```
Asp Pro Tyr Asp Glu Tyr Trp Asn Met Asn Gln Gln Trp Asn Phe Leu
                85                  90                  95

Glu Leu Gln Ala Asn Thr Pro Lys Thr Val Thr Gln Thr Phe Thr Gln
            100                 105                 110

Thr Lys Gly Asp Lys Lys Asn Val Glu Phe Ala Phe His Leu Ala Pro
        115                 120                 125

Asp Lys Thr Thr Ser Glu Ala Gln Asn Pro Ala Ser Phe Gln Pro Ile
    130                 135                 140

Thr Tyr Thr Phe Asp Glu Ile Tyr Ile Gln Asp
145                 150                 155
```

(2) INFORMATION FOR SEQ ID NO:4:

(i) SEQUENCE CHARACTERISTICS:
        (A) LENGTH: 165 amino acids
        (B) TYPE: amino acid
        (D) TOPOLOGY: unknown (ii) MOLECULE TYPE: protein (iii) HYPOTHETICAL: no (xi) SEQUENCE DESCRIPTION: SEQ ID NO:4:

```
Leu Thr Glu Leu Val Ser Asn Gly Thr Phe Asn Gly Gly Thr Val Ser
1               5                   10                  15

Pro Trp Trp Ser Gly Pro Asn Thr Gln Ser Arg Val Glu Asn Ala Arg
            20                  25                  30

Leu Arg Val Asp Val Gly Gly Thr Ala Asn Pro Trp Asp Ala Leu
        35                  40                  45

Ile Gly Gln Asp Ile Pro Leu Val Asn Gly Arg Ala Tyr Thr Leu
    50                  55                  60

Ser Phe Thr Ala Ser Ala Ser Val Ser Thr Thr Val Arg Val Thr Val
65                  70                  75                  80

Gln Leu Glu Ser Ala Pro Tyr Thr Ala Pro Leu Asp Arg Gln Ile Thr
                85                  90                  95

Leu Asp Gly Thr Ser Arg Arg Phe Thr Phe Pro Phe Thr Ser Thr Leu
            100                 105                 110

Ala Thr Gln Ala Gly Gln Val Thr Phe Gln Met Gly Gly Arg Ala Thr
        115                 120                 125

Gly Phe Ser Ala Phe Ile Asp Asp Ile Ser Leu Ala Glu Thr Tyr Glu
    130                 135                 140

Phe Val Phe Thr Ser Asn Val Asp Trp Asp Asp Ala Gln Val Ala Phe
145                 150                 155                 160

Gln Ile Gly Gly Ser
                165
```

(2) INFORMATION FOR SEQ ID NO:5:

(i) SEQUENCE CHARACTERISTICS:
        (A) LENGTH: 139 amino acids
        (B) TYPE: amino acid
        (D) TOPOLOGY: unknown (ii) MOLECULE TYPE: protein (iii) HYPOTHETICAL: no (xi) SEQUENCE DESCRIPTION: SEQ ID NO:5:

```
Val Glu Gln Val Arg Asn Gly Thr Phe Asp Thr Thr Asp Pro Trp
1               5                   10                  15
```

-continued

```
Trp Thr Ser Asn Val Thr Ala Gly Leu Ser Asp Gly Arg Leu Cys Ala
            20                  25                  30

Asp Val Pro Gly Gly Thr Thr Asn Arg Trp Asp Ser Ala Ile Gly Gln
        35                  40                  45

Asn Asp Ile Thr Leu Val Lys Gly Glu Thr Tyr Arg Phe Ser Phe His
    50                  55                  60

Ala Ser Gly Ile Pro Glu Gly His Val Val Arg Ala Val Val Gly Leu
65                  70                  75                  80

Ala Val Ser Pro Tyr Asp Thr Trp Gln Glu Ala Ser Pro Val Leu Thr
                85                  90                  95

Glu Ala Asp Gly Ser Tyr Ser Tyr Thr Phe Thr Ala Pro Val Asp Thr
            100                 105                 110

Thr Gln Gly Gln Val Ala Phe Gln Val Gly Gly Ser Thr Asp Ala Trp
        115                 120                 125

Arg Phe Cys Val Asp Asp Val Ser Leu Leu Gly
    130                 135
```

(2) INFORMATION FOR SEQ ID NO:6:

(i) SEQUENCE CHARACTERISTICS:
        (A) LENGTH: 113 amino acids
        (B) TYPE: amino acid
        (D) TOPOLOGY: unknown (ii) MOLECULE TYPE: protein (iii) HYPOTHETICAL: no (xi) SEQUENCE DESCRIPTION: SEQ ID NO:6:

```
Val Asn Gln Ile Arg Asn Gly Asp Phe Ser Ser Gly Thr Ala Pro Trp
1               5                   10                  15

Trp Gly Thr Glu Asn Ile Gln Leu Asn Val Thr Asp Gly Met Leu Cys
            20                  25                  30

Val Asp Val Pro Gly Gly Thr Val Asn Pro Trp Asp Val Ile Ile Gly
        35                  40                  45

Gln Asp Asp Ile Pro Leu Ile Glu Gly Glu Ser Tyr Ala Phe Ser Phe
    50                  55                  60

Thr Ala Ser Ser Thr Val Pro Val Ser Ile Arg Ala Leu Val Gln Glu
65                  70                  75                  80

Pro Val Glu Pro Trp Thr Thr Gln Met Asp Glu Arg Ala Leu Leu Pro
                85                  90                  95

Gly Glu Asp Glu Pro Trp Thr Phe Cys Leu Asp Asp Val Ala Leu Leu
            100                 105                 110

Gly
```

(2) INFORMATION FOR SEQ ID NO:7:

(i) SEQUENCE CHARACTERISTICS:
        (A) LENGTH: 103 base pairs
        (B) TYPE: nucleic acid
        (C) STRANDEDNESS: double
        (D) TOPOLOGY: circular (ii) MOLECULE TYPE: DNA (iii) HYPOTHETICAL: no (xi) SEQUENCE DESCRIPTION: SEQ ID NO:7:

ATCTAGAAAT AATTTTGTTT AACTTTAAGA AGGAGATATA TCCATGGAAT TCGAGCTCGG    60

```
TACCCGGGGA TCCTCTAGAG TCGACCTGCA GGCATGCAAG CTT                               103

(2) INFORMATION FOR SEQ ID NO:8:

(i) SEQUENCE CHARACTERISTICS:
        (A) LENGTH: 37 base pairs
        (B) TYPE: nucleic acid
        (C) STRANDEDNESS: double
        (D) TOPOLOGY: circular (ii) MOLECULE TYPE: DNA (xi) SEQUENCE DESCRIPTION: SEQ ID NO:8:

TTTAACTTTA AGAAGGAGCT CCTTGATGTC CACCCGC                                      37

(2) INFORMATION FOR SEQ ID NO:9:

(i) SEQUENCE CHARACTERISTICS:
        (A) LENGTH: 4 amino acids
        (B) TYPE: amino acid
        (D) TOPOLOGY: unknown (ii) MOLECULE TYPE: protein (iii) HYPOTHETICAL: no (xi) SEQUENCE DESCRIPTION: SEQ ID NO:9:

Met Ser Thr Arg
 1

(2) INFORMATION FOR SEQ ID NO:10:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

CCCACGCCGA TCGAGGGCAG GCCTGAATTC CAGCTCGGTA CCCGGGGATC CTCTAGAGTC              60

GACCTGCAGG CATGCAAGCT T                                                       81

(2) INFORMATION FOR SEQ ID NO:11:

(i) SEQUENCE CHARACTERISTICS:
        (A) LENGTH: 27 amino acids
        (B) TYPE: amino acid
        (D) TOPOLOGY: unknown (ii) MOLECULE TYPE: protein (iii) HYPOTHETICAL: no (xi) SEQUENCE DESCRIPTION: SEQ ID NO:11:

Pro Thr Pro Ile Glu Gly Arg Pro Glu Phe Gln Leu Gly Thr Arg Gly
 1               5                  10                  15

Ser Ser Arg Val Asp Leu Gln Ala Cys Lys Leu
                20                  25

(2) INFORMATION FOR SEQ ID NO:12:

(i) SEQUENCE CHARACTERISTICS:
        (A) LENGTH: 36 base pairs
        (B) TYPE: nucleic acid
```

```
            (C) STRANDEDNESS: double
            (D) TOPOLOGY: linear (ii) MOLECULE TYPE: DNA (xi) SEQUENCE DESCRIPTION: SEQ ID NO:12:

TTACCTCATA TGGCTAGCCC GATCGGGGAG GGAACG                                      36

(2) INFORMATION FOR SEQ ID NO:13:

(i) SEQUENCE CHARACTERISTICS:
            (A) LENGTH: 36 base pairs
            (B) TYPE: nucleic acid
            (C) STRANDEDNESS: double
            (D) TOPOLOGY: linear (ii) MOLECULE TYPE: DNA (xi) SEQUENCE DESCRIPTION: SEQ ID NO:13:

AGAATGAATT CAAGCTTAGA GCTCGACCTC GGAGTC                                      36

(2) INFORMATION FOR SEQ ID NO:14:

(i) SEQUENCE CHARACTERISTICS:
            (A) LENGTH: 20 amino acids
            (B) TYPE: amino acid
            (D) TOPOLOGY: unknown (ii) MOLECULE TYPE: protein (iii) HYPOTHETICAL: no (xi) SEQUENCE DESCRIPTION: SEQ ID NO:14:

Met Glu Phe Glu Leu Gly Thr Arg Gly Ser Ser Arg Val Asp Leu
 1               5                  10                  15

Gln Ala Cys Lys Leu
            20
```